United States Patent
Gu et al.

(10) Patent No.: US 10,105,431 B2
(45) Date of Patent: Oct. 23, 2018

(54) STREPTOCOCCUS PNEUMONIAE CAPSULAR POLYSACCHARIDES AND CONJUGATES THEREOF

(71) Applicant: Pfizer Inc., New York, NY (US)

(72) Inventors: Jianxin Gu, Paramus, NJ (US); Rajesh Kumar Kainthan, Tappan, NY (US); Jin-Hwan Kim, Suffern, NY (US); Avvari Krishna Prasad, Chapel Hill, NC (US); Yu-Ying Yang, Stamford, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 15/110,634

(22) PCT Filed: Jan. 15, 2015

(86) PCT No.: PCT/IB2015/050314
§ 371 (c)(1),
(2) Date: Jul. 8, 2016

(87) PCT Pub. No.: WO2015/110940
PCT Pub. Date: Jul. 30, 2015

(65) Prior Publication Data
US 2016/0324948 A1 Nov. 10, 2016

Related U.S. Application Data

(60) Provisional application No. 61/929,598, filed on Jan. 21, 2014.

(51) Int. Cl.
| | | |
|---|---|---|
| *A61K 45/06* | (2006.01) | |
| *A61K 47/00* | (2006.01) | |
| *A61K 39/09* | (2006.01) | |
| *A61K 39/385* | (2006.01) | |
| *A61K 39/39* | (2006.01) | |
| *A61K 39/00* | (2006.01) | |

(52) U.S. Cl.
CPC .......... *A61K 39/092* (2013.01); *A61K 39/385* (2013.01); *A61K 39/39* (2013.01); *A61K 2039/55505* (2013.01); *A61K 2039/575* (2013.01); *A61K 2039/6037* (2013.01); *A61K 2039/6068* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 4,709,017 A | 11/1987 | Collier et al. | |
| 4,912,094 A | 3/1990 | Myers | |
| 4,950,740 A | 8/1990 | Greenfield et al. | |
| 5,057,540 A | 10/1991 | Kensil et al. | |
| 5,371,197 A * | 12/1994 | Marburg | A61K 39/092 424/194.1 |
| 5,614,382 A | 3/1997 | Metcalf | |
| 5,843,711 A | 12/1998 | Collier et al. | |
| 5,917,017 A | 6/1999 | Collier et al. | |
| 6,113,918 A | 9/2000 | Johnson et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,455,673 B1 | 9/2002 | Collier | |
| 7,709,001 B2 * | 5/2010 | Hausdorff | A61K 39/092 424/184.1 |
| 7,955,605 B2 * | 6/2011 | Prasad | A61K 39/092 424/184.1 |
| 8,603,484 B2 * | 12/2013 | Prasad | A61K 39/092 424/184.1 |
| 8,753,645 B2 * | 6/2014 | Biemans | A61K 39/092 424/194.1 |
| 8,895,724 B2 * | 11/2014 | Hausdorff | A61K 39/092 424/197.11 |
| 9,265,839 B2 * | 2/2016 | Biemans | A61K 39/092 |
| 9,265,840 B2 * | 2/2016 | Biemans | A61K 39/092 |
| 9,346,861 B2 * | 5/2016 | Dehottay | C07K 14/195 |
| 9,492,559 B2 * | 11/2016 | Emini | A61K 47/4833 |
| 9,517,274 B2 * | 12/2016 | Gu | A61K 47/48261 |
| 9,533,032 B2 * | 1/2017 | Mekalanos | A61K 39/385 |

(Continued)

FOREIGN PATENT DOCUMENTS

| | | |
|---|---|---|
| EP | 0372501 | 6/1990 |
| EP | 0378881 | 7/1990 |

(Continued)

OTHER PUBLICATIONS

Biagini et al, Clinical and diagnostic Laboratory Immunology, Sep. 2003, 101/5:744-750, Method for Simultaneous Measurement of Antibodies to 23 Pneumococcal Capsular Polysaccharides.*

(Continued)

*Primary Examiner* — Nita M. Minnifield
(74) *Attorney, Agent, or Firm* — Keith D. Hutchinson; Matthew J. Pugmire

(57) ABSTRACT

The invention relates to activated *Streptococcus pneumoniae* serotype 10A, 22F or 33F polysaccharides and processes for their preparation. The invention also relates to immunogenic conjugates comprising *Streptococcus pneumoniae* serotype 10A, 22F or 33F polysaccharides covalently linked to a carrier protein, processes for their preparation and immunogenic compositions and vaccines comprising them.

9 Claims, 3 Drawing Sheets

Specification includes a Sequence Listing.

(56) References Cited

U.S. PATENT DOCUMENTS

| | | | |
|---|---|---|---|
| 9,636,392 B2* | 5/2017 | Shin | A61K 39/092 |
| 9,950,054 B2* | 4/2018 | Gu | A61K 47/646 |
| 2003/0147922 A1* | 8/2003 | Capiau | A61K 39/092 424/244.1 |
| 2004/0202668 A1* | 10/2004 | Boutriau | A61K 39/095 424/184.1 |
| 2006/0228380 A1 | 10/2006 | Hausdorff et al. | |
| 2006/0228381 A1 | 10/2006 | Bahler et al. | |
| 2007/0110762 A1* | 5/2007 | Jessouroun | A61K 39/095 424/190.1 |
| 2007/0141084 A1* | 6/2007 | Lee | A61K 39/00 424/236.1 |
| 2007/0184071 A1* | 8/2007 | Hausdorff | A61K 39/092 424/244.1 |
| 2007/0184072 A1* | 8/2007 | Hausdorff | A61K 39/092 424/244.1 |
| 2007/0231340 A1 | 10/2007 | Hausdorff et al. | |
| 2008/0102498 A1 | 5/2008 | Bahler et al. | |
| 2011/0071279 A1* | 3/2011 | Hausdorff | A61K 39/092 530/395 |
| 2012/0301502 A1* | 11/2012 | Caulfield | A61K 39/092 424/197.11 |
| 2012/0321660 A1* | 12/2012 | Biemans | A61K 39/092 424/197.11 |
| 2013/0273098 A1* | 10/2013 | Blue | A61K 33/06 424/197.11 |
| 2014/0186389 A1* | 7/2014 | Biemans | A61K 39/092 424/197.11 |
| 2014/0186390 A1* | 7/2014 | Biemans | A61K 39/092 424/197.11 |
| 2015/0202309 A1* | 7/2015 | Emini | A61K 47/4833 424/450 |
| 2015/0216996 A1* | 8/2015 | Gu | A61K 47/48246 424/194.1 |
| 2016/0136257 A1* | 5/2016 | Mekalanos | A61K 39/385 424/197.11 |
| 2016/0324948 A1* | 11/2016 | Gu | A61K 39/092 |
| 2016/0324949 A1* | 11/2016 | Han | A61K 39/39 |
| 2016/0324950 A1* | 11/2016 | Anderson | C07K 16/1275 |
| 2017/0007713 A1* | 1/2017 | Gu | A61K 39/092 |
| 2017/0021006 A1* | 1/2017 | Watson | A61K 47/6415 |
| 2018/0000922 A1* | 1/2018 | Cooper | A61K 39/092 |
| 2018/0099039 A1* | 4/2018 | Emini | A61K 39/092 |

FOREIGN PATENT DOCUMENTS

| | | | |
|---|---|---|---|
| EP | 0427347 | 5/1991 | |
| EP | 0471177 | 2/1992 | |
| EP | 0594610 | 5/1994 | |
| WO | WO9014837 | 12/1990 | |
| WO | WO9101146 | 2/1991 | |
| WO | WO9219265 | 11/1992 | |
| WO | WO9313302 | 7/1993 | |
| WO | WO9317712 | 9/1993 | |
| WO | WO9403208 | 2/1994 | |
| WO | WO9858668 | 12/1998 | |
| WO | WO0018434 | 4/2000 | |
| WO | WO0037105 | 6/2000 | |
| WO | WO0039299 | 7/2000 | |
| WO | WO0056357 | 9/2000 | |
| WO | WO0061761 | 10/2000 | |
| WO | WO0172337 | 10/2001 | |
| WO | WO0198334 | 12/2001 | |
| WO | WO02091998 | 11/2002 | |
| WO | WO02098368 | 12/2002 | |
| WO | WO02098369 | 12/2002 | |
| WO | WO03024480 | 3/2003 | |
| WO | WO03054007 | 7/2003 | |
| WO | WO2004081515 | 9/2004 | |
| WO | WO2005033148 | 4/2005 | |
| WO | WO2007026190 | 3/2007 | |
| WO | WO2008118752 | 10/2008 | |
| WO | WO2008157590 | 12/2008 | |
| WO | WO2009000826 | 12/2008 | |
| WO | WO2010125480 | 11/2010 | |
| WO | WO-2011110531 A2 * | 9/2011 | A61K 39/092 |
| WO | WO-2014097099 A2 * | 6/2014 | A61K 47/4833 |
| WO | WO-2015110940 A2 * | 7/2015 | A61K 39/092 |
| WO | WO-2016178123 A1 * | 11/2016 | C07K 16/1275 |

OTHER PUBLICATIONS

Trotter et al, Vaccine 26 (2008) 4434-4445, Optimising the use of conjugate vaccines to prevent disease caused by Haemophilus influenzae type b, Neisseria meningitidis and *Streptococcus pneumoniae*.*

Gerritzen et al, Biotechnology Advances 35 (2017) 565-574 "Bioengineering bacterial outer membrane vesicles as vaccine platform".*

Kuo et al, Infection and Immunity, Jul. 1995, 63/7:2706-2713 "Characterization of a Recombinant Pneumolysin and Its Use as a Protein Carrier for Pneumococcal Type 18C Conjugate Vaccines".*

The C-Type Lectin SIGN-R1 Mediates Uptake of the Capsular Polysaccharide of*Streptococcus pneumoniae* in the Marginal Zone of Mouse SpleenAuthor(s): Young-Sun Kang, Jae Y. Kim, Sandra A. Bruening, Maggi Pack, Anna Charalambous, Alla Pritsker, Thomas M. Moran, Jutta M. Loeffler, Ralph M. Steinman and Chae Gyu ParkSource: Proceedings of the National Academy of Sciences of the United States of America,vol. 101, No. 1 (Jan. 6, 2004), pp. 215-220Published by: National Academy of SciencesStable URL: http://www.jstor.org/stable/3148400.*

Analytical Biochemistry 358 (2006) 136-142www.elsevier.com/locate/yabio0003-2697/$—see front matter © 2006 Elsevier Inc. All rights reserved.doi:10.1016/j.ab.2006.08.016Monitoring activation sites on polysaccharides by GC-MSJohn S. Kima,¤, Erin R. Laskowich a, Francis Michon b, Raymond E. Kaiser a,Rasappa G. Arumugham a.*

Baraldo, K., et al., "N19 Polyepitope as a Carrier for Enhanced Immunogenicity and Protective Efficacy of Meningococcal Conjugate Vaccines", Infection and Immunity, 2004, vol. 72, No. 8, 4884-4887.

Crooke, S.T., et al., "Progress in Antisense Oligonucleotide Therapeutics" Annual Review of Pharmacology and Toxicology, Apr. 1996, pp. 107-129, vol. 36.

Doe, B., et al., "Induction of HIV-1 envelope (gp120)-specific cytotoxic T lymphocyte responses in mice by recombinant CHO cell-derived gp120 is enhanced by enzymatic removal of N-linked glycans", Eur. J. Immunol., 1994, 24:2369-2376.

Erickson, A., et al., "Hepatitis C Virus-Specific CTL Responses in the Liver of Chimpanzees with Acute and Chronic Hepatitis C", The Journal of Immunology, 1993, pp. 4189-4199, vol. 151, No. 8.

Falugi, F., et al., "Rationally designed strings of promiscuous CD4+ T cell epitopes provide help to Haemophilus influenzae type b oligosaccharide: a model for new conjugate vaccines," Eur. J. Immunology, 2001, vol. 31, 3816-3824.

Hestrin, S., "The Reaction of Acetylcholine and other Carboxylic Acid Derivatives with Hydroxylamine, and its Analytical Application", J. Biol. Chem., 1949, 180:249-261.

Hu, B., et al., "Approach to Validating an Opsonophagocytic Assay for *Strepto coccus pneumoniae*", Clin. and Diag. Lab. Immun. 2005, p. 287-295, vol. 12, No. 2.

Hunziker, J., et al., "Nucleic Acid Analogues: Synthesis and Properties", Modem Synthesis Methods, 1995, pp. 331-417, vol. 7.

Jones, C., et al., "Use and validation of NMR assays for the identity and O-acetyl content of capsular polysaccharides from Neisseria meningitidis used in vaccine manufacture", Journal of Pharm. and Biomed. Anal., 2002, 30:1233-1247.

Kuo, J., et al., "Characterization of a Recombinant Pneumolysin and Its Use as a Protein Carrier for Pneumococcal Type 18C Conjugate Vaccines," Infection and Immunity, 1995, vol. 63, No. 7, 2706-2713.

Lemercinier, X., et al., "Full 1H NMR assignment and detailed O-acetylation patterns of capsular polysaccharides from Neisseria meningitidis used in vaccine production", Carbohydrate Research, 1996, 296:83-96.

(56) References Cited

OTHER PUBLICATIONS

Uchida, T., et al., "Diphtheria Toxin and Related Proteins," The Journal of Biological Chemistry, 1973, vol. 248, No. 11, 3838-3844.

Uchida, T., et al., "Mutation in the Structural Gene for Diphtheria Toxin carried by Temperate Phage," Nature New Biology, 1971, 9-11, vol. 233.

Uhlmann, E., et al., "Antisense Oligonucleotides: A New Therapeutic Principle", Chemical Reviews, Jun. 1990, pp. 543-584, vol. 90, No. 4.

Biagini, R., et al., "Method for Simultaneous Measurement of Antibodies to 23 Pneumococcal Capsular Polysaccharides", Clinical and Diagnostic Laboratory Immunology, 2003, 744-750, vol. 10, No. 5.

Frasch, C., "Preparation of bacterial polysaccharide-protein conjugates: Analytical and manufacturing challenges", 2000, Vaccine, 27 (2009) 6468-6470.

Kamerling, J., " Pneumococcal Polysaccharides: A Chemical View", 2000, *Streptococcus pneumoniae*, Mary Ann Liebert, Inc., 81-114.

International Search Report, PCT/IB2015/050314, dated Jan. 15, 2015.

\* cited by examiner

SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: "A class" CpG oligonucleotide

<400> SEQUENCE: 1
ggggacgacg tcgtgggggg g                                                  21

<210> SEQ ID NO 2

```
<211> LENGTH: 21
<212> TYPE: DNA
<213> ORGANISM: Artificial Sequence
<220> FEATURE:
<223> OTHER INFORMATION: "A class" CpG oligonucleotide

<400> SEQUENCE: 2
ggggacgacg tcgtggggggg g                                              21

<210> SEQ ID NO 3
<211> LENGTH: 21
<212> TYPE: DNA
<213> ORGANISM: Artificial Sequence
<220> FEATURE:
<223> OTHER INFORMATION: "B class" CpG oligonucleotide

<400> SEQUENCE: 3
tcgtcgtttt tcggtgcttt t                                               21

<210> SEQ ID NO 4
<211> LENGTH: 21
<212> TYPE: DNA
<213> ORGANISM: Artificial Sequence
<220> FEATURE:
<223> OTHER INFORMATION: "B class" CpG oligonucleotide

<400> SEQUENCE: 4
tcgtcgtttt tcggtcgttt t                                               21

<210> SEQ ID NO 5
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 5
tcgtcgtttt gtcgttttgt cgtt                                            24

<210> SEQ ID NO 6
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 6
tcgtcgtttc gtcgttttgt cgtt                                            24

<210> SEQ ID NO 7
<211> LENGTH: 24
<212> TYPE: DNA
<213> ORGANISM: Artificial Sequence
<220> FEATURE:
<223> OTHER INFORMATION: "B class" CpG oligonucleotide

<400> SEQUENCE: 7
tcgtcgtttt gtcgtttttt tcga                                            24

<210> SEQ ID NO 8
<211> LENGTH: 21
<212> TYPE: DNA
<213> ORGANISM: Artificial Sequence
<220> FEATURE:
<223> OTHER INFORMATION: B-Class oligonucleotide

<400> SEQUENCE: 8
```

```
tcgtcgtttt tcggtgcttt t                                              21

<210> SEQ ID NO 9
<211> LENGTH: 21
<212> TYPE: DNA
<213> ORGANISM: Artificial Sequence
<220> FEATURE:
<223> OTHER INFORMATION: B-Class oligonucleotide

<400> SEQUENCE: 9
tcgtcgtttt tcggtcgttt t                                              21

<210> SEQ ID NO 10
<211> LENGTH: 24
<212> TYPE: DNA
<213> ORGANISM: Artificial Sequence
<220> FEATURE:
<223> OTHER INFORMATION: B-Class oligonucleotide

<400> SEQUENCE: 10
tcgtcgtttt gtcgttttgt cgtt                                           24

<210> SEQ ID NO 11
<211> LENGTH: 24
<212> TYPE: DNA
<213> ORGANISM: Artificial Sequence
<220> FEATURE:
<223> OTHER INFORMATION: B-Class oligonucleotide

<400> SEQUENCE: 11
tcgtcgtttc gtcgttttgt cgtt                                           24

<210> SEQ ID NO 12
<211> LENGTH: 24
<212> TYPE: DNA
<213> ORGANISM: Artificial Sequence
<220> FEATURE:
<223> OTHER INFORMATION: B-Class oligonucleotide

<400> SEQUENCE: 12
tcgtcgtttt gtcgtttttt tcga                                           24

<210> SEQ ID NO 13
<211> LENGTH: 22
<212> TYPE: DNA
<213> ORGANISM: Artificial Sequence
<220> FEATURE:
<223> OTHER INFORMATION: C class CpG Oligonucleotide

<400> SEQUENCE: 13
tcgcgtcgtt cggcgcgcgc cg                                             22

<210> SEQ ID NO 14
<211> LENGTH: 23
<212> TYPE: DNA
<213> ORGANISM: Artificial Sequence
<220> FEATURE:
<223> OTHER INFORMATION: C class CpG Oligonucleotide

<400> SEQUENCE: 14
tcgtcgacgt tcggcgcgcg ccg                                            23

<210> SEQ ID NO 15
<211> LENGTH: 21
<212> TYPE: DNA
```

<213> ORGANISM: Artificial Sequence
<220> FEATURE:
<223> OTHER INFORMATION: C class CpG Oligonucleotide

<400> SEQUENCE: 15
tcggacgttc ggcgcgcgcc g                                    21

<210> SEQ ID NO 16
<211> LENGTH: 19
<212> TYPE: DNA
<213> ORGANISM: Artificial Sequence
<220> FEATURE:
<223> OTHER INFORMATION: C class CpG Oligonucleotide

<400> SEQUENCE: 16
tcggacgttc ggcgcgccg                                       19

<210> SEQ ID NO 17
<211> LENGTH: 20
<212> TYPE: DNA
<213> ORGANISM: Artificial Sequence
<220> FEATURE:
<223> OTHER INFORMATION: C class CpG Oligonucleotide

<400> SEQUENCE: 17
tcgcgtcgtt cggcgcgccg                                      20

<210> SEQ ID NO 18
<211> LENGTH: 20
<212> TYPE: DNA
<213> ORGANISM: Artificial Sequence
<220> FEATURE:
<223> OTHER INFORMATION: C class CpG Oligonucleotide

<400> SEQUENCE: 18
tcgacgttcg gcgcgcgccg                                      20

<210> SEQ ID NO 19
<211> LENGTH: 18
<212> TYPE: DNA
<213> ORGANISM: Artificial Sequence
<220> FEATURE:
<223> OTHER INFORMATION: C class CpG Oligonucleotide

<400> SEQUENCE: 19
tcgacgttcg gcgcgccg                                        18

<210> SEQ ID NO 20
<211> LENGTH: 18
<212> TYPE: DNA
<213> ORGANISM: Artificial Sequence
<220> FEATURE:
<223> OTHER INFORMATION: C class CpG Oligonucleotide

<400> SEQUENCE: 20
tcgcgtcgtt cggcgccg                                        18

<210> SEQ ID NO 21
<211> LENGTH: 22
<212> TYPE: DNA
<213> ORGANISM: Artificial Sequence
<220> FEATURE:
<223> OTHER INFORMATION: C class CpG Oligonucleotide

<400> SEQUENCE: 21
tcgcgacgtt cggcgcgcgc cg                                   22

<210> SEQ ID NO 22
<211> LENGTH: 22
<212> TYPE: DNA
<213> ORGANISM: Artificial Sequence
<220> FEATURE:
<223> OTHER INFORMATION: C class CpG Oligonucleotide

<400> SEQUENCE: 22
tcgtcgtttt cggcgcgcgc cg                                    22

<210> SEQ ID NO 23
<211> LENGTH: 22
<212> TYPE: DNA
<213> ORGANISM: Artificial Sequence
<220> FEATURE:
<223> OTHER INFORMATION: C class CpG Oligonucleotide

<400> SEQUENCE: 23
tcgtcgtttt cggcggccgc cg                                    22

<210> SEQ ID NO 24
<211> LENGTH: 24
<212> TYPE: DNA
<213> ORGANISM: Artificial Sequence
<220> FEATURE:
<223> OTHER INFORMATION: C class CpG Oligonucleotide

<400> SEQUENCE: 24
tcgtcgtttt acggcgccgt gccg                                  24

<210> SEQ ID NO 25
<211> LENGTH: 23
<212> TYPE: DNA
<213> ORGANISM: Artificial Sequence
<220> FEATURE:
<223> OTHER INFORMATION: C class CpG Oligonucleotide

<400> SEQUENCE: 25
tcgtcgtttt cggcgcgcgc cgt                                   23

<210> SEQ ID NO 26
<211> LENGTH: 22
<212> TYPE: DNA
<213> ORGANISM: Artificial Sequence
<220> FEATURE:
<223> OTHER INFORMATION: C-Class oligonucleotides

<400> SEQUENCE: 26
tcgcgtcgtt cggcgcgcgc cg                                    22

<210> SEQ ID NO 27
<211> LENGTH: 23
<212> TYPE: DNA
<213> ORGANISM: Artificial Sequence
<220> FEATURE:
<223> OTHER INFORMATION: C-Class oligonucleotide

<400> SEQUENCE: 27
tcgtcgacgt tcggcgcgcg ccg                                   23

<210> SEQ ID NO 28
<211> LENGTH: 21
<212> TYPE: DNA
<213> ORGANISM: Artificial Sequence
<220> FEATURE:

```
<223> OTHER INFORMATION: C-Class oligonucleotide

<400> SEQUENCE: 28
tcggacgttc ggcgcgcgcc g                                             21

<210> SEQ ID NO 29
<211> LENGTH: 19
<212> TYPE: DNA
<213> ORGANISM: Artificial Sequence
<220> FEATURE:
<223> OTHER INFORMATION: C-Class oligonucleotide

<400> SEQUENCE: 29
tcggacgttc ggcgcgccg                                                19

<210> SEQ ID NO 30
<211> LENGTH: 20
<212> TYPE: DNA
<213> ORGANISM: Artificial Sequence
<220> FEATURE:
<223> OTHER INFORMATION: C-Class oligonucleotide

<400> SEQUENCE: 30
tcgcgtcgtt cggcgcgccg                                               20

<210> SEQ ID NO 31
<211> LENGTH: 20
<212> TYPE: DNA
<213> ORGANISM: Artificial Sequence
<220> FEATURE:
<223> OTHER INFORMATION: C-Class oligonucleotide

<400> SEQUENCE: 31
tcgacgttcg gcgcgcgccg                                               20

<210> SEQ ID NO 32
<211> LENGTH: 18
<212> TYPE: DNA
<213> ORGANISM: Artificial Sequence
<220> FEATURE:
<223> OTHER INFORMATION: C-Class oligonucleotide

<400> SEQUENCE: 32
tcgacgttcg gcgcgccg                                                 18

<210> SEQ ID NO 33
<211> LENGTH: 18
<212> TYPE: DNA
<213> ORGANISM: Artificial Sequence
<220> FEATURE:
<223> OTHER INFORMATION: C-Class oligonucleotide

<400> SEQUENCE: 33
tcgcgtcgtt cggcgccg                                                 18

<210> SEQ ID NO 34
<211> LENGTH: 22
<212> TYPE: DNA
<213> ORGANISM: Artificial Sequence
<220> FEATURE:
<223> OTHER INFORMATION: C-Class oligonucleotide

<400> SEQUENCE: 34
tcgcgacgtt cggcgcgcgc cg                                            22
```

```
<210> SEQ ID NO 35
<211> LENGTH: 22
<212> TYPE: DNA
<213> ORGANISM: Artificial Sequence
<220> FEATURE:
<223> OTHER INFORMATION: C-Class oligonucleotide

<400> SEQUENCE: 35
tcgtcgtttt cggcgcgcgc cg                                              22

<210> SEQ ID NO 36
<211> LENGTH: 22
<212> TYPE: DNA
<213> ORGANISM: Artificial Sequence
<220> FEATURE:
<223> OTHER INFORMATION: C-Class oligonucleotide

<400> SEQUENCE: 36
tcgtcgtttt cggcggccgc cg                                              22

<210> SEQ ID NO 37
<211> LENGTH: 24
<212> TYPE: DNA
<213> ORGANISM: Artificial Sequence
<220> FEATURE:
<223> OTHER INFORMATION: C-Class oligonucleotide

<400> SEQUENCE: 37
tcgtcgtttt acggcgccgt gccg                                            24

<210> SEQ ID NO 38
<211> LENGTH: 23
<212> TYPE: DNA
<213> ORGANISM: Artificial Sequence
<220> FEATURE:
<223> OTHER INFORMATION: C-Class oligonucleotide

<400> SEQUENCE: 38
tcgtcgtttt cggcgcgcgc cgt                                             23

<210> SEQ ID NO 39
<211> LENGTH: 23
<212> TYPE: DNA
<213> ORGANISM: Artificial Sequence
<220> FEATURE:
<223> OTHER INFORMATION: P class CpG oligonucleotide

<400> SEQUENCE: 39
tcgtcgacga tcggcgcgcg ccg                                             23

<210> SEQ ID NO 40
<211> LENGTH: 23
<212> TYPE: DNA
<213> ORGANISM: Artificial Sequence
<220> FEATURE:
<223> OTHER INFORMATION: P class CpG oligonucleotide

<400> SEQUENCE: 40
tcgtcgacga tcggcgcgcg ccg                                             23
```

STREPTOCOCCUS PNEUMONIAE CAPSULAR POLYSACCHARIDES AND CONJUGATES THEREOF

CROSS REFERENCE TO RELATED APPLICATIONS

This application is a National Stage Application of International Application No. PCT/IB2015/050314, filed Jan. 15, 2015, which claims the benefit under 35 U.S.C. § 119(e) of U.S. Provisional Application Ser. No. 61/929,598, filed Jan. 21, 2014, both of which are incorporated by reference in their entirety.

REFERENCE TO SEQUENCE LISTING

This application is being filed electronically via EFS-Web and includes an electronically submitted sequence listing in .txt format. The .txt file contains a sequence listing entitled "PC71942A_Sequence_Listing_ST25.txt", created on Jun. 30, 2016 and having a size of 8.04 KB. The sequence listing contained in this .txt file is part of the specification and is herein incorporated by reference in its entirety.

FIELD OF THE INVENTION

The invention relates to activated *Streptococcus pneumoniae* serotype 10A, 22F or 33F polysaccharides and processes for their preparation. The invention also relates to immunogenic conjugates comprising *Streptococcus pneumoniae* serotype 10A, 22F or 33F polysaccharides covalently linked to a carrier protein, processes for their preparation and immunogenic compositions and vaccines comprising them.

BACKGROUND

*Streptococcus pneumoniae* are Gram-positive, lancet shaped cocci that are usually seen in pairs (diplococci), but also in short chains or as single cells. They grow readily on blood agar plates with glistening colonies and display alpha hemolysis unless grown anaerobically where they show beta hemolysis. The cells of most pneumococcal serotypes have a capsule which is a polysaccharide coating surrounding each cell. This capsule is a determinant of virulence in humans, as it interferes with phagocytosis by preventing antibodies from attaching to the bacterial cells. Currently there are more than 90 known pneumococcal capsular serotypes identified, with the 23 most common serotypes accounting for approximately 90% of invasive disease worldwide. As a vaccine, the pneumococcal polysaccharide coat can confer a reasonable degree of immunity to *Streptococcus pneumoniae* in individuals with developed or unimpaired immune systems, but the capsular polysaccharide conjugated to a suitable carrier protein allows for an immune response in infants and elderly who are also at most risk for pneumococcal infections.

Since the introduction of the first 7-valent pneumococcal conjugate vaccine (PCV7 or Prevnar) in 2000, invasive disease from those seven serotypes (4, 6B, 9V, 14, 18C, 19F, and 23F) has nearly disappeared. The addition of serotypes 1, 3, 5, 6A, 7F and 19A in Prevnar 13 further decreased the numbers of invasive pneumococcal disease.

None of the currently marketed pneumococcal vaccine provides an appropriate protection against serotype 10A, 22F or 33F *Streptococcus pneumoniae* in human and in particular in children less than 2 years old. Therefore, there is a need for immunogenic compositions that can be used to induce an immune response against serotype 10A, 22F or 33F *Streptococcus pneumonia*.

SUMMARY OF THE INVENTION

In one aspect the present disclosure provides a process for preparing an activated *Streptococcus pneumoniae* serotype 10A, 22F or 33F capsular polysaccharide, the process comprising the steps of:

(a) reacting an isolated serotype 10A, 22F or 33F capsular polysaccharide with an oxidizing agent; and;

(b) quenching the oxidation reaction by addition of a quenching agent resulting in an activated *Streptococcus pneumoniae* serotype 10A, 22F or 33F polysaccharide.

In a further aspect, the invention relates to activated *Streptococcus pneumoniae* serotype 10A, 22F or 33F capsular polysaccharide obtained or obtainable by the activation process disclosed herein.

In a further aspect, the present disclosure provides a process for the preparation of an immunogenic conjugate comprising *Streptococcus pneumoniae* serotype 10A, 22F or 33F polysaccharide covalently linked to a carrier protein, the process comprising the steps of:

(a) compounding an activated serotype 10A, 22F or 33F polysaccharide obtained or obtainable by a process disclosed herein with a carrier protein; and, (b) reacting the compounded, activated serotype 10A, 22F or 33F polysaccharide and carrier protein with a reducing agent to form a serotype 10A, 22F or 33F polysaccharide:carrier protein conjugate.

In a further aspect, the present disclosure provides serotype 10A, 22F or 33F polysaccharide:carrier protein conjugate obtained or obtainable by the process disclosed herein.

In a further aspect, the present disclosure provides immunogenic compositions and vaccines comprising immunogenic conjugate disclosed herein.

In a further aspect, the present disclosure a method of treating or preventing a *Streptococcus pneumoniae* infection, disease or condition associated with serotype 10A, 22F or 33F *Streptococcus pneumoniae* in a subject, the method comprising the step of administering a therapeutically or prophylactically effective amount of an immunogenic composition or a vaccine disclosed herein.

DETAILED DESCRIPTION OF THE INVENTION

Figure 1:
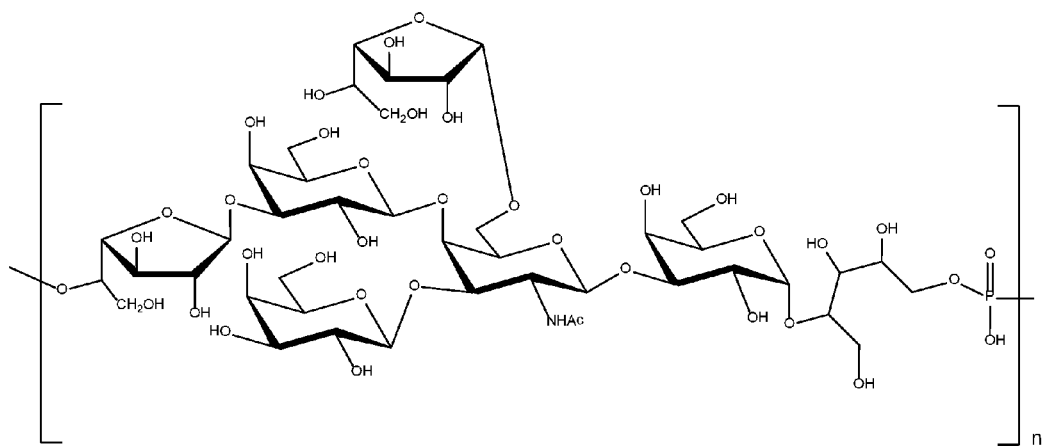
FIG. 1 shows the structure of *Streptococcus pneumoniae* capsular polysaccharide Serotype 10A Repeat Unit.

The present invention may be understood more readily by reference to the following detailed description of the preferred embodiments of the invention and the Examples included herein. Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, certain preferred methods and materials are described herein. In describing the embodiments and claiming the invention, certain terminology will be used in accordance with the definitions set out below.

As used herein, the singular forms "a", "an", and "the" include plural references unless indicated otherwise. Thus, for example, references to "the method" includes one or more methods, and/or steps of the type described herein and/or which will become apparent to one of ordinary skill in the art upon reading this disclosure.

As used herein, the term "molecular weight" of polysaccharide or of carrier protein-polysaccharide conjugate refers to molecular weight calculated by size exclusion chromatography (SEC) combined with multiangle laser light scattering detector (MALLS).

As used herein, the term "degree of oxidation" (DO) refers to the number of sugar repeat units per aldehyde group generated when the isolated polysaccharide is activated with an oxidizing agent. The degree of oxidation of a polysaccharide can be determined using routine methods known to the man skilled in the art.

It is noted that in this disclosure, terms such as "comprises," "comprised," "comprising," "contains," "containing" and the like can have the meaning attributed to them in U.S. patent law; e.g., they can mean "includes," "included," "including" and the like. Such terms refer to the inclusion of a particular ingredients or set of ingredients without excluding any other ingredients. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from the novel or basic characteristics of the invention. The terms "consists of" and "consisting of" have the meaning ascribed to them in U.S. patent law; namely, that these terms are closed ended. Accordingly, these terms refer to the inclusion of a particular ingredient or set of ingredients and the exclusion of all other ingredients.

As used herein, the term "conjugates" or "glycoconjugates" as used herein refers to a polysaccharide covalently conjugated to a carrier protein. Glycoconjugates of the invention and immunogenic compositions comprising them may contain some amount of free polysaccharide.

As used herein, the term "serotype 10A glycoconjugate" or "serotype 10A conjugate" refers to an isolated *Streptococcus pneumoniae* serotype 10A capsular polysaccharide covalently conjugated to a carrier protein.

As used herein, the term "serotype 22F glycoconjugate" or "serotype 22F conjugate" refers to an isolated *Streptococcus pneumoniae* serotype 22F capsular polysaccharide covalently conjugated to a carrier protein.

As used herein, the term "serotype 33F glycoconjugate" or "serotype 33F conjugate" refers to an isolated *Streptococcus pneumoniae* serotype 33F capsular polysaccharide covalently conjugated to a carrier protein.

As used herein, the term "serotype 10A polysaccharide" refers to a *Streptococcus pneumoniae* serotype 10A capsular polysaccharide.

As used herein, the term "serotype 22F polysaccharide" refers to a *Streptococcus pneumoniae* serotype 22F capsular polysaccharide.

As used herein, the term "serotype 33F polysaccharide" refers to a *Streptococcus pneumoniae* serotype 33F capsular polysaccharide.

As used herein, the term "free polysaccharide" means a capsular polysaccharide that is not covalently conjugated to the carrier protein, but is nevertheless present in the capsular polysaccharide-carrier protein conjugate composition. The free polysaccharide may be non-covalently associated with (i.e., non-covalently bound to, adsorbed to, or entrapped in or with) the polysaccharide-carrier protein conjugate.

The percentage of free polysaccharide is measured after the final purification of the serotype 10A, 22F or 33F capsular polysaccharide-carrier protein conjugate. Preferably it is measured within 4 weeks after the final purification. It is expressed as a percentage of the total polysaccharide in the sample.

As used herein, "to conjugate," "conjugated" and "conjugating" refer to a process whereby a *Streptococcus pneumoniae* capsular polysaccharide, is covalently attached to a carrier protein.

The term "subject" refers to a mammal, including a human, or to a bird, fish, reptile, amphibian or any other animal. The term "subject" also includes household pets or research animals. Non-limiting examples of household pets and research animals include: dogs, cats, pigs, rabbits, rats, mice, gerbils, hamsters, guinea pigs, ferrets, monkeys, birds, snakes, lizards, fish, turtles, and frogs. The term "subject" also includes livestock animals. Non-limiting examples of livestock animals include: alpaca, bison, camel, cattle, deer, pigs, horses, llamas, mules, donkeys, sheep, goats, rabbits, reindeer, yak, chickens, geese, and turkeys.

In the preparation of multivalent conjugate pneumococcal vaccines directed to the prevention of invasive diseases caused by the organism *Streptococcus pneumoniae* (also known as pneumococcus), selected *Streptococcus pneumoniae* serotypes are grown to supply polysaccharides needed to produce the vaccine. The cells are grown in fermentors with lysis induced at the end of the fermentation by addition of sodium deoxycholate or an alternate lysing agent. The lysate broth is then harvested for downstream purification and the recovery of the capsular polysaccharide which surrounds the bacterial cells. After activation and conjugation with a carrier protein, the polysaccharide is included in the final vaccine product and confers immunity in the vaccine's target population to the selected *Streptococcus pneumoniae* serotypes.

The immunogenicity of a polysaccharide:carrier protein conjugate depends on several factors including the size of the polysaccharide. Polysaccharide size is a quality attribute assayed for in each preparation batch and must be appropriately controlled. High molecular weight capsular polysaccharides are able to induce certain antibody immune responses due to a higher valence of the epitopes present on the antigenic surface. It is generally preferable to prevent or to limit undesirable reduction of the size of the polysaccharide during the preparation of the conjugate to retain the immunogenicity of the polysaccharide. In addition, it is important to reduce the batch to batch variability of the polysaccharide Molecular Weight during the activation step and subsequent conjugation in order to maintain the consistency of the quality attributes of the conjugate.

Reductive amination chemistry (RAC) has been demonstrated by the inventors as a suitable process for preparing the *Streptococcus pneumoniae* serotype 10A, 22F or 33F capsular polysaccharide-protein carrier conjugate. The RAC approach involves activation of the polysaccharide by oxidation and subsequent conjugation of the activated polysaccharide to a protein carrier by reduction. Serotype 10A, 33F and 22F polysaccharides have proven to be particularly sensitive polysaccharides and are susceptible to degradation and size reduction during the oxidation step of the preparation of the conjugate. In addition, the use of hitherto known activation process produced activated serotype 10A, 33F and 22F polysaccharide of variable molecular weights.

Therefore, there is an important need for a process for preparing activated *Streptococcus pneumoniae* serotype 10A, 22F or 33F polysaccharides having a controlled and consistent molecular weight.

An object of the present invention is a process for preparing activated *Streptococcus pneumoniae* serotype 10A, 22F or 33F polysaccharides. In particular, an object of the invention is a process for preparing an activated *Streptococcus pneumoniae* serotype 10A, 22F or 33F polysaccharide, said process comprising the steps of:

(a) reacting isolated serotype 10A, 22F or 33F polysaccharide with an oxidizing agent; and, (b) quenching the oxidation reaction by addition of a quenching agent resulting in an activated *Streptococcus pneumoniae* serotype 10A, 22F or 33F polysaccharide.

Isolation and Purification of Serotype 10A, 22F or 33F Polysaccharide

The structures of serotype 10A, 22F and 33F polysaccharides are disclosed in the literature (see for example Kamerling J P C. Pneumococcal polysaccharides: a chemical view. In: Tomasz A, editor. *Streptococcus pneumoniae*, molecular biology and mechanisms of disease. New York, N.Y.: Mary Ann Liebert, Inc.; 2000. pp. 81-114).

As shown in FIG. 1, the polysaccharide repeating unit of serotype 22F consists of a branched pentasaccharide backbone (one glucuronic acid (GlcpA), one glucopyranose (Glcp) and one galactofuranose (Galf) and two rhamnopyranoses (Rhap)) with a αGlcp branch linked to the C3 hydroxyl group of βRhap 45. Approximately 80% of the C2 hydroxyl groups of the βRhap residue in the polysaccharide repeating unit are O-acetylated.

Figure 2:
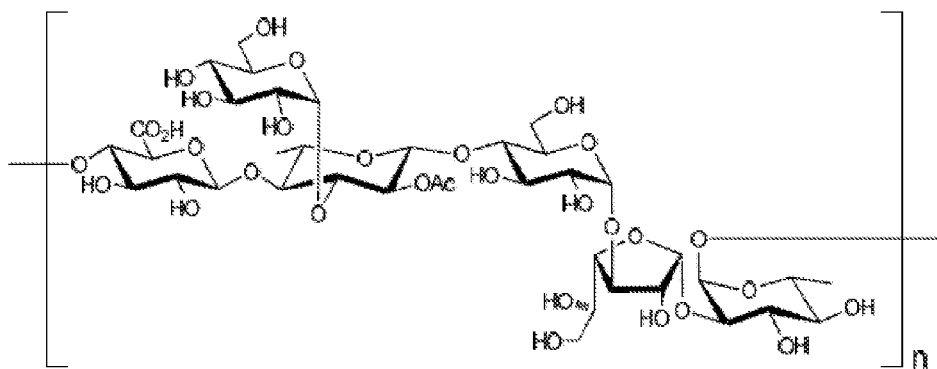
FIG. 2 shows the structure of *Streptococcus pneumoniae* capsular polysaccharide Serotype 22F Repeat Unit.

As shown in FIG. 2, the polysaccharide repeating unit of serotype 10A consists of a two D-galactosefuranose, three D-galactopyranose, one N-acetylgalactosamine, and a phosphate bond linked with saccharide chain through one D-ribitol.

Figure 3:
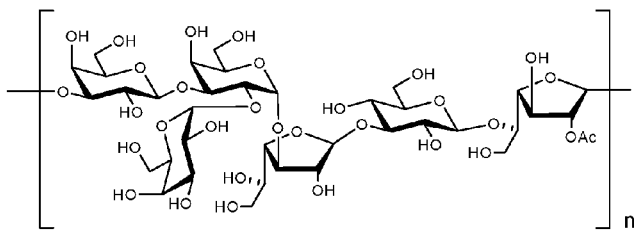
FIG. 3 shows the structure of *Streptococcus pneumoniae* capsular polysaccharide Serotype 33F Repeat Unit.

As shown in FIG. 3, the polysaccharide repeating unit of serotype 33F consists of three $_D$-galactopyranose, two D-galactofuranose, and one D-glucopyranose. Notably, 5-D-galactofuranosyl residues are O-acetylated in about 90% of 33F polysaccharide repeating units.

Serotype 10A, 22F and 33F capsular polysaccharides can be obtained directly from bacteria using isolation procedures known to one of ordinary skill in the art (see for example methods disclosed U.S. Patent App. Pub. Nos. 20060228380, 20060228381, 20070184071, 20070184072, 20070231340, and 20080102498 or WO2008118752). In addition, they can be produced using synthetic protocols.

Serotype 10A, 22F and 33F *Streptococcus pneumoniae* strains used to make the respective polysaccharides that are used in the immunogenic conjugates of the invention may be obtained from established culture collections or clinical specimens.

The purified serotype 10A, 22F and 33F polysaccharides are obtained by methods well known to the man skilled in the art. The bacterial cells are preferably grown in a soy based medium. Following fermentation of bacterial cells that produce *Streptococcus pneumoniae* serotype 10A, 22F or 33F capsular polysaccharides, the bacterial cells are lysed to produce a cell lysate. The bacterial cells may be lysed using any lytic agent. A "lytic agent" is any agent that aids in cell wall breakdown and release of autolysin which causes cellular lysis including, for example, detergents. As used herein, the term "detergent" refers to any anionic or cationic detergent capable of inducing lysis of bacterial cells. Representative examples of such detergents for use within the methods of the present invention include deoxycholate sodium (DOC), N-lauroyl sarcosine, chenodeoxycholic acid sodium, and saponins.

In one embodiment of the present invention, the lytic agent used for lysing bacterial cells is DOC. DOC is the sodium salt of the bile acid deoxycholic acid, which is commonly derived from biological sources such as cows or oxen. DOC activates the LytA protein, which is an autolysin that is involved in cell wall growth and division in *Streptococcus pneumoniae*. The LytA protein has choline binding domains in its C-terminal portion, and mutations of the lytA gene are known to produce LytA mutants that are resistant to lysis with DOC.

In one embodiment of the present invention, the lytic agent used for lysing bacterial cells is a non-animal derived lytic agent. Non-animal derived lytic agents for use within the methods of the present invention include agents from non-animal sources with modes of action similar to that of DOC (i. e., that affect LytA function and result in lysis of *Streptococcus pneumoniae* cells). Such non-animal derived lytic agents include, but are not limited to, analogs of DOC, surfactants, detergents, and structural analogs of choline. In one embodiment, the non-animal derived lytic agent is selected from the group consisting of decanesulfonic acid, tert-octylphenoxy poly(oxyethylene)ethanols (e.g. Igepal® CA-630, CAS #: 9002-93-1, available from Sigma Aldrich, St. Louis, Mo.), octylphenol ethylene oxide condensates (e.g. Triton® X-100, available from Sigma Aldrich, St. Louis, Mo.), N-lauroyl sarcosine sodium, lauryl iminodipropionate, sodium dodecyl sulfate, chenodeoxycholate, hyodeoxycholate, glycodeoxycholate, taurodeoxycholate, taurochenodeoxycholate, and cholate. In another embodiment, the non-animal derived lytic agent is N-lauroyl sarcosine. In another embodiment, the lytic agent is N-lauroyl sarcosine sodium.

The capsular polysaccharides may then be purified from the cell lysate using purification techniques known in the art, including the use of centrifugation, depth filtration, precipitation, ultra-filtration, treatment with activate carbon, diafiltration and/or column chromatography (See, for example, U.S. Patent App. Pub. Nos. 20060228380, 20060228381, 20070184071, 20070184072, 20070231340, and 20080102498 or WO2008118752). The purified serotype 10A, 22F or 33F polysaccharides can then be used for the preparation of immunogenic conjugates.

Preferably, in order to generate serotype 22F conjugates or serotype 33F conjugates with advantageous filterability characteristics and/or yields, sizing of the polysaccharide to a lower molecular weight (MW) range is performed prior to the conjugation to a carrier protein. Advantageously, the size of the purified serotype 22F polysaccharide or serotype 33F polysaccharide is reduced while preserving critical features of the structure of the polysaccharide such as for example the presence of O-acetyl groups. Preferably, the size of the purified serotype 22F polysaccharide or serotype 33F polysaccharide is reduced by mechanical homogenization.

In a preferred embodiment, the size of the purified polysaccharide is reduced by high pressure homogenization.

High pressure homogenization achieves high shear rates by pumping the process stream through a flow path with sufficiently small dimensions. The shear rate is increased by using a larger applied homogenization pressure and exposure time can be increased by recirculating the feed stream through the homogenizer.

The high pressure homogenization process is particularly appropriate for reducing the size of the purified serotype 22F polysaccharide or serotype 33F polysaccharide while preserving the structural features of the polysaccharide such as the presence of O-acetyl groups.

The isolated serotype 22F polysaccharide obtained by purification of serotype 22F capsular polysaccharide from the Streptococcus pneumoniae lysate and optionally sizing of the purified polysaccharide can be characterized by different parameters including for example the molecular weight, and the mM of acetate per mM of serotype 22F polysaccharide. In a preferred embodiment, the sized serotype 22F polysaccharide has a molecular weight comprised between 400 and 700 kDa.

The isolated serotype 33F polysaccharide obtained by purification of serotype 33F capsular polysaccharide from the Streptococcus pneumoniae lysate and optionally sizing of the purified polysaccharide can be characterized by different parameters including for example the molecular weight, and the mM of acetate per mM of serotype 33F polysaccharide.

The degree of O-acetylation of the polysaccharide can be determined by any method known in the art, for example, by proton NMR (Lemercinier and Jones (1996) Carbohydrate Research 296; 83-96, Jones and Lemercinier (2002) J. Pharmaceutical and Biomedical Analysis 30; 1233-1247, WO 05/033148 or WO00/56357. Another commonly used method is described in Hestrin (1949) J. Biol. Chem. 180; 249-261. Preferably, the presence of O-acetyl groups is determined by ion-HPLC analysis.

In a preferred embodiment, the isolated serotype 22F polysaccharide is obtained by a process comprising the steps of:
preparing a fermentation culture of serotype 22F Streptococcus pneumonia bacterial cells;
lysing the bacterial cells in said fermentation culture; and,
purifying serotype 22F polysaccharide from the fermentation culture.

In a preferred embodiment, the isolated serotype 22F polysaccharide is obtained by a process comprising the steps of:
preparing a fermentation culture of serotype 22F Streptococcus pneumonia bacterial cells;
lysing the bacterial cells in said fermentation culture;
purifying serotype 22F polysaccharide from the fermentation culture; and,
sizing the serotype 22F polysaccharide by mechanical sizing, preferably by high pressure homogenization.

In a preferred embodiment, the isolated serotype 22F polysaccharide is obtained by a process comprising the steps of:
preparing a fermentation culture of serotype 22F Streptococcus pneumonia bacterial cells;
lysing the bacterial cells in said fermentation culture;
purifying serotype 22F polysaccharide from the fermentation culture; and,
sizing the serotype 22F polysaccharide by mechanical sizing, preferably by high pressure homogenization, wherein the isolated serotype 22F polysaccharide has a molecular weight comprised between 400 and 700 kDa.

In a preferred embodiment, the isolated serotype 33F polysaccharide is obtained by a process comprising the steps of:
preparing a fermentation culture of serotype 33F Streptococcus pneumonia bacterial cells;
lysing the bacterial cells in said fermentation culture; and,
purifying serotype 33F polysaccharide from the fermentation culture.

In a preferred embodiment, the isolated serotype 33F polysaccharide is obtained by a process comprising the steps of:
preparing a fermentation culture of serotype 33F Streptococcus pneumonia bacterial cells;
lysing the bacterial cells in said fermentation culture;
purifying serotype 33F polysaccharide from the fermentation culture; and,
sizing the serotype 33F polysaccharide by mechanical sizing, preferably by high pressure homogenization.

The isolated serotype 10A polysaccharide obtained by purification of serotype 10A capsular polysaccharide from the Streptococcus pneumoniae lysate and optionally sizing of the purified polysaccharide can be characterized by different parameters including for example the molecular weight. Preferably, the isolated serotype 10A polysaccharide is not sized.

In a preferred embodiment, the isolated serotype 10A polysaccharide is obtained by a process comprising the steps of:
preparing a fermentation culture of serotype 10A Streptococcus pneumonia bacterial cells;
lysing the bacterial cells in said fermentation culture; and,
purifying serotype 10A polysaccharide from the fermentation culture.

Activation of Serotype 10A, 22F or 33F Polysaccharide

The isolated serotype 10A, 22F or 33F polysaccharide is activated by a process comprising the step of:
(a) reacting an isolated serotype 10A, 22F or 33F polysaccharide with an oxidizing agent; and,
(b) quenching the oxidation reaction by addition of a quenching agent resulting in an activated Streptococcus pneumoniae serotype 10A, 22F or 33F polysaccharide.

In a preferred embodiment, the concentration of serotype 10A, 22F or 33F polysaccharide in step (a) is between 0.1 and 10 mg/mL. In a preferred embodiment, the concentration of serotype 10A, 22F or 33F polysaccharide in step (a) is between 0.5 and 5 mg/mL. In a preferred embodiment, the concentration of serotype 10A, 22F or 33F polysaccharide in step (a) is between 1 and 3 mg/mL. In a preferred embodiment, the concentration of serotype 22F or 33F polysaccharide in step (a) is about 2 mg/mL. In a preferred embodiment, the concentration of serotype 10A polysaccharide in step (a) is about 2.5 mg/mL.

In a preferred embodiment, the oxidizing agent is periodate. The periodate oxidises vicinal hydroxyl groups to form carbonyl or aldehyde groups and causes cleavage of a C—C bond. The term 'periodate' includes both periodate and periodic acid. This term also includes both metaperiodate ($IO_4^-$) and orthoperiodate ($IO_6^{5-}$). The term 'periodate' also includes the various salts of periodate including sodium periodate and potassium periodate. In a preferred embodiment, the oxidizing agent is sodium periodate. In a preferred embodiment, the periodate used for the oxidation of serotype 10A, 22F or 33F polysaccharide is metaperiodate. In a preferred embodiment the periodate used for the oxidation of serotype 10A, 22F or 33F polysaccharide is sodium metaperiodate.

In a preferred embodiment, the polysaccharide is reacted with 0.01 to 10, 0.05 to 5, 0.1 to 1, 0.5 to 1, 0.7 to 0.8, 0.01 to 0.2, 0.05 to 0.5, 0.05 to 0.2, 0.1 to 0.3 molar equivalents of oxidizing agent. In a preferred embodiment, the polysaccharide is reacted with about 0.05, 0.1, 0.15, 0.2, 0.25, 0.3, 0.35, 0.4, 0.45, 0.5, 0.55, 0.6, 0.65, 0.7, 0.75, 0.8, In a preferred embodiment, the polysaccharide is reacted with about 0.10 molar equivalent of oxidizing agent. In a preferred embodiment, the polysaccharide is reacted with about 0.15 molar equivalent of oxidizing agent. In a preferred embodiment, the polysaccharide is reacted with about 0.25 molar equivalent of oxidizing agent. In a preferred embodiment, the polysaccharide is reacted with about 0.5 molar equivalent of oxidizing agent. In a preferred embodiment, the polysaccharide is reacted with about 0.8 molar equivalent of oxidizing agent.

In a preferred embodiment, the duration of the reaction in step (a) is between 1 and 50, 1 and 40, 1 and 30, 1 and 25, 1 and 20, 1 and 10, 10 to 50, 10 to 40, 10 to 30, 10 to 20 hours. In a preferred embodiment, when the polysaccharide is serotype 10A polysaccharide, the duration of the reaction in step (a) is between 1 to 10 hours. In a preferred embodiment, when the polysaccharide is serotype 10A polysaccharide, the duration of the reaction in step (a) is about 1, 2, 3, 4, 5, 6, 7, 8, 9, 10 hours. In a preferred embodiment, when the polysaccharide is serotype 10A polysaccharide, the duration of the reaction in step (a) is about 4 hours. In a preferred embodiment, when the polysaccharide is serotype 22F polysaccharide, the duration of the reaction in step (a) is between 10 and 20 hours. In a preferred embodiment, when the polysaccharide is serotype 22F polysaccharide, the duration of the reaction in step (a) is about 10, 11, 12, 13, 14, 15, 16, 17, 18, 19, 20 hours. In a preferred embodiment, when the polysaccharide is serotype 33F polysaccharide, the duration of the reaction in step (a) is between 15 to 25 hours. In a preferred embodiment, when the polysaccharide is serotype 33F polysaccharide, the duration of the reaction in step (a) is about 15, 16, 17, 18, 19, 20, 21, 22, 23, 24 or 25 hours. In a preferred embodiment, when the polysaccharide is serotype 33F polysaccharide, the duration of the reaction in step (a) is about 20 hours.

In a preferred embodiment, the temperature of the reaction in step (a) is maintained between 1 to 30° C., 1 to 10° C., 10 to 20° C., 20 to 30° C., 2 to 8° C. In a preferred embodiment, the temperature of the reaction in step (a) is maintained at about 5° C.

In a preferred embodiment, step (a) is carried out in a buffer selected from sodium phosphate, potassium phosphate, 2-(N-morpholino)ethanesulfonic acid (MES) or Bis-Tris. In a preferred embodiment step (a) is carried out in potassium phosphate buffer. In a preferred embodiment step (a) is carried out in sodium phosphate buffer.

In a preferred embodiment the buffer has a concentration of between 1 to 500 mM, 1 to 300 mM, 50 to 200 mM. In a preferred embodiment the buffer has a concentration of about 100 mM.

In a preferred embodiment the pH in step (a) is between 4 and 8, 5 and 7, 5.5 and 6.5. In a preferred embodiment the pH in step (a) is about 6. In a preferred embodiment the pH in step (a) is about 5.8.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula

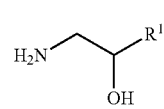

(I)

where $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid.

In one embodiment, the quenching agent is an amino acid. In one embodiment, said amino acid is selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e two hydroxyl groups covalently linked to two adjacent carbon atoms.

Preferably, the quenching agent is a compound of formula (II)

(II)

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, ascorbic acid. In a preferred embodiment, the quenching agent is butan-2,3-diol.

In a preferred embodiment, the oxidizing agent is neutralized by the addition of 0.1 to 10, 0.5 to 5, 0.5 to 3, 0.5 to 2 molar equivalents of quenching agent. In a preferred embodiment, the oxidizing agent is neutralized by the addition of about 0.5, 1, 1.5, 2, 2.5, 3 molar equivalents of quenching agent. In a preferred embodiment, the oxidizing agent is neutralized by the addition of about 2 molar equivalents of quenching agent.

In a preferred embodiment, the duration of step (b) is between 0.1 and 10, 0.5 and 5, or 0.5 and 2 hours. In a preferred embodiment, the duration of step (b) is about 0.5, 1, 1.5, 2.5 or 3 hours.

In a preferred embodiment, the temperature of the reaction in step (b) is maintained between 1 and 30° C., 1 and 25° C., 1 and 20° C., 1 and 10° C., 10 and 20° C., 2 and 8° C. In a preferred embodiment, the temperature of the reaction in step (b) is maintained at about 1, 2, 3, 4, 5, 6, 7 or 8° C.

In a preferred embodiment the pH in step (b) is between 4 and 8, 5 and 7, 5.5 and 6.5. In a preferred embodiment the pH in step (a) is about 6.

In a preferred embodiment, the activated serotype 10A, 22F or 33F polysaccharide is purified. The activated serotype 10A, 22F or 33F polysaccharide can be purified according to methods known to the man skilled in the art such as gel permeation chromatography (GPC), dialysis or ultrafiltration/diafiltration. For example, the activated polysaccharide is purified by concentration and diafiltration using an ultrafiltration device.

In preferred embodiment, the isolated serotype 10A polysaccharide is activated by a process comprising the step of:
(a) reacting isolated serotype 10A polysaccharide with periodate; and,
(b) quenching the oxidation reaction by addition of butan-2,3-diol resulting in an activated serotype 10A polysaccharide.

In preferred embodiment, the isolated serotype 10A polysaccharide is activated by a process comprising the step of:
(a) reacting isolated serotype 10A polysaccharide with periodate at a temperature between 2 and 8° C.; and,
(b) quenching the oxidation reaction by addition of butan-2,3-diol at a temperature between 2 and 8° C. resulting in an activated serotype 10A polysaccharide.

In preferred embodiment, the isolated serotype 10A polysaccharide is activated by a process comprising the step of:
(a) reacting isolated serotype 10A polysaccharide with 0.2 to 0.3 molar equivalent periodate at a temperature between 2 and 8° C.; and,
(b) quenching the oxidation reaction by addition of 0.5 to 2 molar equivalent of butan-2,3-diol at a temperature between 2 and 8° C. resulting in an activated serotype 10A polysaccharide.

In preferred embodiments, the isolated serotype 22F polysaccharide is activated by a process comprising the step of:
(a) reacting isolated serotype 22F polysaccharide with periodate; and,
(b) quenching the oxidation reaction by addition of butan-2,3-diol resulting in an activated serotype 22F polysaccharide.

In preferred embodiment, the isolated serotype 22F polysaccharide is activated by a process comprising the step of:
(a) reacting isolated serotype 22F polysaccharide with periodate at a temperature between 2 and 8° C.; and,
(b) quenching the oxidation reaction by addition of butan-2,3-diol at a temperature between 2 and 8° C. resulting in an activated serotype 22F polysaccharide.

In preferred embodiment, the isolated serotype 22F polysaccharide is activated by a process comprising the step of:
(a) reacting isolated serotype 22F polysaccharide with 0.05 to 0.2 molar equivalent periodate at a temperature between 2 and 8° C.; and,
(b) quenching the oxidation reaction by addition of 2 to 3, preferably 2, molar equivalents of butan-2,3-diol at a temperature between 2 and 8° C. resulting in an activated serotype 22F polysaccharide.

In preferred embodiment, the isolated serotype 33F polysaccharide is activated by a process comprising the step of:
(a) reacting isolated serotype 33F polysaccharide with periodate; and,
(b) quenching the oxidation reaction by addition of butan-2,3-diol resulting in an activated serotype 33F polysaccharide.

In preferred embodiment, the isolated serotype 33F polysaccharide is activated by a process comprising the step of:
(a) reacting isolated serotype 33F polysaccharide with periodate at a temperature between 2 and 8° C.; and,
(b) quenching the oxidation reaction by addition of butan-2,3-diol at a temperature between 2 and 8° C. resulting in an activated serotype 33F polysaccharide.

In preferred embodiment, the isolated serotype 33F polysaccharide is activated by a process comprising the step of:
(a) reacting isolated serotype 33F polysaccharide with 0.05 to 0.2 molar equivalent periodate at a temperature between 2 and 8° C.; and,
(b) quenching the oxidation reaction by addition of 0.5 to 1.5 molar equivalent of butan-2,3-diol at a temperature between 2 and 8° C. resulting in an activated serotype 33F polysaccharide.

In a preferred embodiment, the invention relates to an activated serotype 10A capsular polysaccharide obtained or obtainable by the above disclosed process.

In a preferred embodiment, the invention relates to an activated serotype 22F capsular polysaccharide obtained or obtainable by the above disclosed process.

In a preferred embodiment, the invention relates to an activated serotype 33F capsular polysaccharide obtained or obtainable by the above disclosed process.

In a preferred embodiment the activated serotype 10A polysaccharide obtained from step (b) has a molecular weight between 20 and 100%, 30 and 95%, 40 and 95%, 60 to 95%, 85 to 95%, or about 90%, of the molecular weight of the isolated polysaccharide used in step (a).

In a preferred embodiment the activated serotype 10A polysaccharide obtained from step (b) has a molecular weight of at least 20, 25, 30, 35, 40 or 45% of the molecular weight of the isolated polysaccharide used in step (a). In a preferred embodiment the activated serotype 10A polysaccharide obtained from step (b) has a molecular weight of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% of the molecular weight of the isolated polysaccharide used in step (a).

In a preferred embodiment the activated serotype 22F polysaccharide obtained from step (b) has a molecular weight between 50 and 100%, 60 to 95%, 85 to 95% or about 90% of the molecular weight of the isolated polysaccharide used in step (a).

In a preferred embodiment the activated serotype 22F polysaccharide obtained from step (b) has a molecular weight of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% of the molecular weight of the isolated polysaccharide used in step (a).

In a preferred embodiment the activated serotype 33F polysaccharide obtained from step (b) has a molecular weight between 50 and 100%, 60 to 95%, 85 to 95%, or about 90% of the molecular weight of the isolated polysaccharide used in step (a).

In a preferred embodiment the activated serotype 33F polysaccharide obtained from step (b) has a molecular weight of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% of the molecular weight of the isolated polysaccharide used in step (a).

In a preferred embodiment the degree of oxidation of the activated serotype 10A, 22F or 33F polysaccharide is between 2 and 30, 2 and 25, 2 and 20, 2 and 15, 2 and 10, 2 and 5, 5 and 30, 5 and 25, 5 and 20, 5 and 15, 5 and 10, 10 and 30, 10 and 25, 10 and 20, 10 and 15, 5 and 25, 10 and 30, 15 and 30, 15 and 25, 15 and 20, 20 to 30, 20 to 25. In a preferred embodiment the degree of oxidation of the activated serotype 10A, 22F or 33F polysaccharide is between 2 and 10, 4 and 8, 4 and 6, 6 and 8, 6 and 12, 8 and 14, 9 and 11, 10 and 16, 12 and 16, 14 and 18, 16 and 20, 16 and 18, 18 and 22, 18 and 20.

In a preferred embodiment, the activated serotype 10A polysaccharide has a molecular weight between 50 and 400, 50 and 350, 50 and 300, 50 and 250, 50 and 200, 100 and 300, 100 and 250 or 100 and 200 kDa. In a preferred embodiment, the activated serotype 10A polysaccharide has a molecular weight between 50 and 300 kDa. In a preferred embodiment, the activated serotype 10A polysaccharide has a molecular weight between 100 and 200 kDa. In a preferred embodiment, the activated serotype 10A polysaccharide has a molecular weight between 100 and 200 kDa and a degree of oxidation between 5 and 20, 5 and 15, 8 and 14, 8 and 12 or 9 and 11. In a preferred embodiment, the activated serotype 10A polysaccharide has a molecular weight between 100 and 200 kDa and a degree of oxidation between 9 and 11.

In a preferred embodiment, the activated serotype 22F polysaccharide has a molecular weight between 25 and 1000, 100 and 1000, 300 and 800, 300 and 700, 300 and 600, 400 and 1000, 400 and 800, 400 and 700 or 400 and 600 kDa. In a preferred embodiment, the activated serotype 22F polysaccharide has a molecular weight between 300 and 800 kDa. In a preferred embodiment, the activated serotype 22F polysaccharide has a molecular weight between 400 and 800 kDa. In a preferred embodiment, the activated serotype 22F polysaccharide has a molecular weight between 400 and 600 kDa. In a preferred embodiment, the activated serotype 22F polysaccharide has a molecular weight between 400 and 800 kDa and a degree of oxidation between 10 and 25, 10 and 20, 12 and 20 or 14 and 18. In a preferred embodiment, the activated serotype 22F polysaccharide has a molecular weight between 400 and 800 kDa and a degree of oxidation between 10 and 20.

In a preferred embodiment, the activated serotype 22F polysaccharide comprises at least 0.1, 0.2, 0.3, 0.4, 0.5, 0.6 or 0.7 or about 0.8 mM acetate per mM serotype 22F polysaccharide. In a preferred embodiment, the activated serotype 22F polysaccharide comprises at least 0.5, 0.6 or 0.7 mM acetate per mM serotype 22F polysaccharide. In a preferred embodiment, the activated serotype 22F polysaccharide comprises at least 0.6 mM acetate per mM serotype 22F polysaccharide. In a preferred embodiment, the activated serotype 22F polysaccharide comprises at least 0.7 mM acetate per mM serotype 22F polysaccharide.

In a preferred embodiment, the activated serotype 22F polysaccharide has a molecular weight between 400 and 800 kDa and comprises at least 0.6 mM acetate per mM serotype 22F polysaccharide.

In a preferred embodiment, the activated serotype 22F polysaccharide has a molecular weight between 400 and 800 kDa, a degree of oxidation between 12 and 20 and comprises at least 0.6 mM acetate per mM serotype 22F polysaccharide.

In a preferred embodiment, the activated serotype 33F polysaccharide has a molecular weight between 50 and 1250, 200 and 1200, 500 and 1200, 500 and 1000, 700 and 1200, 800 and 1200, 800 and 1100, 900 and 1200, 800 and 1000 Da. In a preferred embodiment, the activated serotype 33F polysaccharide has a molecular weight between 500 and 1000 kDa. In another preferred embodiment, the activated serotype 33F polysaccharide has a molecular weight between 50 and 600, 50 and 500 or 50 and 400 kDa.

In a preferred embodiment, the activated serotype 33F polysaccharide comprises at least 0.1, 0.2, 0.3, 0.4, 0.5, 0.6, 0.7 or 0.8 or about 0.9 mM acetate per mM serotype 33F polysaccharide. In a preferred embodiment, the activated serotype 33F polysaccharide comprises at least 0.6, 0.7 or 0.8 mM acetate per mM serotype 33F polysaccharide. In a preferred embodiment, the activated serotype 33F polysaccharide comprises at least 0.6 mM acetate per mM serotype 33F polysaccharide. In a preferred embodiment, the activated serotype 33F polysaccharide comprises at least 0.7 mM acetate per mM serotype 33F polysaccharide.

In a preferred embodiment, the activated serotype 33F polysaccharide has a molecular weight between 800 and 1200 kDa and comprises at least 0.7 mM acetate per mM serotype 33F polysaccharide. In a preferred embodiment, the activated serotype 33F polysaccharide has a molecular weight between 800 and 1200 kDa, comprises at least 0.7 mM acetate per mM serotype 33F polysaccharide and has a degree of oxidation between 10 and 20.

In a preferred embodiment, the activated serotype 33F polysaccharide has a molecular weight between 50 and 200 kDa and comprises at least 0.7 mM acetate per mM serotype 33F polysaccharide.

In a preferred embodiment, the activated serotype 33F polysaccharide has a molecular weight between 50 and 200 kDa, comprises at least 0.7 mM acetate per mM serotype 33F polysaccharide and has a degree of oxidation between 10 and 20.

In an embodiment, the activated serotype 10A, 22F or 33F polysaccharide is lyophilized, optionally in the presence of a cryoprotectant/lyoprotectant. In a preferred embodiment, the cryoprotectant/lyoprotectant is selected from sucrose, trehalose, raffinose, stachyose, melezitose, dextran, mannitol, lactitol and palatinit. In a preferred embodiment, the cryoprotectant/lyoprotectant is sucrose. The lyophilized activated polysaccharide can then be compounded with a solution comprising the carrier protein.

In another embodiment, the activated serotype 10A, 22F or 33F polysaccharide is compounded with the carrier protein and lyophilized optionally in the presence of a cryoprotectant/lyoprotectant. In a preferred embodiment, the cryoprotectant/lyoprotectant is selected from sucrose, trehalose, raffinose, stachyose, melezitose, dextran, mannitol, lactitol and palatinit. In a preferred embodiment, the cryoprotectant/lyoprotectant is sucrose. The co-lyophilized polysaccharide and carrier protein can then be resuspended in solution and reacted with a reducing agent.

In an embodiment, the invention relates to a lyophilized activated serotype 10A polysaccharide. In an embodiment, the invention relates to a lyophilized activated serotype 22F polysaccharide. In an embodiment, the invention relates to a lyophilized activated serotype 33F polysaccharide.

In an embodiment the invention relates to the co-lyophilized activated serotype 10A polysaccharide and protein carrier. In a preferred embodiment, the protein carrier is $CRM_{197}$.

In an embodiment the invention relates to the co-lyophilized activated serotype 22F polysaccharide and protein carrier. In a preferred embodiment, the protein carrier is $CRM_{197}$.

In an embodiment the invention relates to the co-lyophilized activated serotype 33F polysaccharide and protein carrier. In a preferred embodiment, the protein carrier is $CRM_{197}$.

Conjugation of Activated Serotype 10A, 22F or 33F Polysaccharide with a Carrier Protein The activated serotype 10A, 22F or 33F polysaccharide disclosed herein can be conjugated to a carrier protein by a process comprising the steps of:
 (a) compounding the activated serotype 10A, 22F or 33F polysaccharide with a carrier protein; and,
 (b) reacting the compounded activated serotype 10A, 22F or 33F polysaccharide and carrier protein with a reducing agent to form a serotype 10A, 22F or 33F polysaccharide: carrier protein conjugate.

The conjugation of activated serotype 22F or 33F polysaccharide with a protein carrier by reductive amination in dimethylsulfoxide (DMSO) is suitable to preserve the O-acetyl content of the polysaccharide as compared for example to reductive amination in aqueous phase where the level of O-acetylation of the polysaccharide is significantly reduced. In a preferred embodiment, step (a) and step (b) are carried out in DMSO.

In a preferred embodiment, step (a) comprises dissolving lyophilized serotype 10A, 22F or 33F polysaccharide in an aqueous solution comprising a carrier protein or in a solution comprising a carrier protein and DMSO. In a preferred embodiment, step (a) comprises dissolving co-lyophilized serotype 10A, 22F or 33F polysaccharide and carrier protein in an aqueous solution or in DMSO.

When step (a) and (b) are carried out in an aqueous solution, said solution comprises a buffer, preferably selected from buffer, preferably selected from PBS, MES, HEPES, Bis-tris, ADA, PIPES. MOPSO, BES, MOPS, DIPSO, MOBS, HEPPSO, POPSO, TEA, EPPS, Bicine or HEPB, at a pH between 6.0 and 8.5, 7 and 8 or 7 and 7.5. In a preferred embodiment the buffer is PBS. In a preferred embodiment the pH is about 7.3.

In a preferred embodiment, the concentration of activated serotype 10A, 22F or 33F polysaccharide in step (a) is between 0.1 and 10 mg/mL, 0.5 and 5 mg/mL, 0.5 and 2 mg/mL. In a preferred embodiment, the concentration of activated serotype 10A, 22F or 33F polysaccharide in step (a) is about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 mg/mL.

In a preferred embodiment the initial ratio (weight by weight) of activated serotype 10A, 22F or 33F polysaccharide to carrier protein is between 5:1 and 0.1:1, 2:1 and 0.1:1, 2:1 and 1:1, 1.5:1 and 1:1, 0.1:1 and 1:1, 0.3:1 and 1:1, 0.6:1 and 1:1.2. In a preferred embodiment the initial ratio of activated serotype 10A, 22F or 33F polysaccharide to carrier protein is about 0.6:1 and 1:1.2. In a preferred embodiment the initial ratio of activated serotype 10A, 22F or 33F polysaccharide to carrier protein is about 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1.

In a preferred embodiment, in step (b), the activated serotype 10A, 22F or 33F polysaccharide is reacted with between 0.1 and 10 molar equivalents, 0.5 and 5 molar equivalents 0.5 and 2.5 molar equivalents of reducing agent. In a preferred embodiment, in step (b), the activated serotype 10A, 22F or 33F is reacted with about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4 or 2.5 molar equivalents of reducing agent.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—BH$_3$, benzylamine-BH$_3$ or 5-ethyl-2-methylpyridine borane (PEMB). In a preferred embodiment, the reducing agent is sodium cyanoborohydride.

In a preferred embodiment, the duration of step (b) is between 1 and 50, 5 and 30, 10 and 30, 15 and 30, 20 and 30, 5 and 25, 10 and 25, 15 and 25 hours. In a preferred embodiment, the duration of step (b) is about 20, 21, 22, 23, 24, 25, 26, 27, 28 hours.

In a preferred embodiment, the temperature of the reaction in step (b) is maintained between 10 and 40° C., 15 and 30° C., 20 and 26° C., 21 and 25° C. In a preferred embodiment, the temperature of the reaction in step (b) is maintained at about 21, 22, 23, 24 or 25° C.

In a preferred embodiment, the process for the preparation of an immunogenic conjugate comprising serotype 10A, 22F or 33F polysaccharide covalently linked to a carrier protein further comprises a step (step c) of capping unreacted aldehyde (quenching) by addition of NaBH$_4$.

In a preferred embodiment, in step (c), the unreacted aldehydes are capped by the addition of 0.1 to 10 molar equivalents, 0.5 to 5 molar equivalents or 1 to 3 molar equivalents of NaBH$_4$. In a preferred embodiment, in step (c), the unreacted aldehydes are capped by the addition of about 2 molar equivalents of NaBH$_4$.

In a preferred embodiment, the duration of step (c) is between 0.1 and 10, 0.5 and 5 or 2 and 4 hours. In a preferred embodiment, the duration of step (c) is about 3 hours.

In a preferred embodiment, the temperature of the reaction in step (c) is maintained between 10 to 40° C., 15 to 30° C. or 20 to 26° C. In a preferred embodiment, the temperature of the reaction in step (c) is maintained at about 23° C.

After conjugation of serotype 10A, 22F or 33F polysaccharide to the carrier protein, the polysaccharide-protein conjugate can be purified (enriched with respect to the amount of polysaccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

In a preferred embodiment the carrier protein is non-toxic and non-reactogenic and obtainable in sufficient amount and purity. Carrier proteins should be amenable to standard conjugation procedures.

In a preferred embodiment, the activated serotype 10A, 22F or 33F polysaccharide is conjugated to a carrier protein which is selected in the group consisting of: DT (Diphtheria toxin), TT (tetanus toxid) or fragment C of TT, CRM197 (a nontoxic but antigenically identical variant of diphtheria toxin) other DT point mutants, such as CRM176, CRM228, CRM 45 (Uchida et al J. Biol. Chem. 218; 3838-3844, 1973); CRM 9, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711, pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE (sequences of PhtA, PhtB, PhtD or PhtE are disclosed in WO 00/37105 or WO 00/39299) and fusions of Pht proteins for example PhtDE fusions, PhtBE fusions, Pht A-E (WO 01/98334, WO 03/54007, W02009/000826), OMPC (meningococcal outer membrane protein—usually extracted from *N. meningitidis* serogroup B—EP0372501), PorB (from *N. meningitidis*), PD (*Haemophilus influenza* protein D—see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471 177), cytokines, lymphokines, growth factors or hormones (WO10 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761). In an embodiment, the activated serotype 10A, 22F or 33F polysaccharide is conjugated to DT (Diphtheria toxoid). In another embodiment, the activated serotype 10A, 22F or 33F polysaccharide is conjugated to TT (tetanus toxid). In another embodiment, the activated serotype 10A, 22F or 33F polysaccharide is conjugated to fragment C of TT. In another embodiment, the activated serotype 10A, 22F or 33F polysaccharide is conjugated to PD (*Haemophilus influenza* protein D—see, e.g., EP 0 594 610 B).

In a preferred embodiment, the activated serotype 10A, 22F or 33F polysaccharide is conjugated to $CRM_{197}$ protein. The $CRM_{197}$ protein is a nontoxic form of diphtheria toxin but is immunologically indistinguishable from the diphtheria toxin. $CRM_{197}$ is produced by *C. diphtheriae* infected by the nontoxigenic phage $\beta 197^{tox-}$ created by nitrosoguanidine mutagenesis of the toxigenic corynephage beta (Uchida, T. et al. 1971, Nature New Biology 233:8-11). $CRM_{197}$ is purified through ultrafiltration, ammonium sulfate precipitation, and ion-exchange chromatography. The $CRM_{197}$ protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The $CRM_{197}$ protein is a safe and effective T-cell dependent carrier for saccharides. Further details about $CMR_{197}$ and production thereof can be found e.g. in U.S. Pat. No. 5,614,382.

In a preferred embodiment, the activated serotype 10A, 22F or 33F polysaccharide disclosed herein is conjugated to $CRM_{197}$ by a process comprising the step of:
 (a) compounding the activated serotype 10A, 22F or 33F polysaccharide with $CRM_{197}$;
 (b) reacting the compounded activated serotype 10A, 22F or 33F polysaccharide and $CRM_{197}$ with sodium cyanoborohydride to form a serotype 10A, 22F or 33F polysaccharide:CRM197 conjugate.

In a preferred embodiment, the activated serotype 10A, 22F or 33F polysaccharide disclosed herein is conjugated to CRM197 by a process comprising the step of:
 (a) compounding the activated serotype 10A, 22F or 33F polysaccharide with a $CRM_{197}$;
 (b) reacting the compounded activated serotype 10A, 22F or 33F polysaccharide and $CRM_{197}$ with sodium cyanoborohydride to form a serotype 10A, 22F or 33F polysaccharide: CRM197 conjugate;
 wherein steps (a) and (b) are carried out in DMSO.

In a preferred embodiment, the activated serotype 10A, 22F or 33F polysaccharide disclosed herein is conjugated to $CRM_{197}$ by a process comprising the step of:
 (a) compounding the activated serotype 10A, 22F or 33F polysaccharide with a $CRM_{197}$;
 (b) reacting the compounded activated serotype 10A, 22F or 33F polysaccharide and $CRM_{197}$ with 0.5 to 2 molar equivalent sodium cyanoborohydride to form a serotype 10A, 22F or 33F polysaccharide:$CRM_{197}$ conjugate;
 wherein steps (a) and (b) are carried out in DMSO.

In an embodiment, the invention relates to an immunogenic conjugate obtained or a obtainable by a process disclosed herein. In a preferred embodiment, the invention relates to an immunogenic conjugate obtained or obtainable by conjugating a serotype 10A, 22F or 33F activated polysaccharide as disclosed herein to a carrier protein by reductive amination. In a preferred embodiment, the invention relates to an immunogenic conjugate obtained or obtainable by conjugating a serotype 10A, 22F or 33F activated polysaccharide as disclosed herein to a carrier protein by reductive amination in DMSO. In a preferred embodiment, the carrier protein is $CRM_{197}$.

Serotype 10A Immunogenic Conjugate

In a preferred embodiment, the serotype 10A immunogenic conjugate has a molecular weight between 500 and 15000; 500 and 10000; 2000 and 10000; or 3000 and 8000 kDa. In a preferred embodiment, the serotype 10A immunogenic conjugate has a molecular weight between 3000 and 8000 kDa. The molecular weight of the immunogenic conjugate is measured by SEC-MALLS.

In a preferred embodiment, the serotype 10A immunogenic conjugate comprises less than about 50, 45, 40, 35, 30, 25, 20 or 15% of free serotype 10A polysaccharide compared to the total amount of serotype 10A polysaccharide. In a preferred embodiment the serotype 10A immunogenic conjugate comprises less than about 25% of free serotype 10A polysaccharide compared to the total amount of serotype 10A polysaccharide. In a preferred embodiment the serotype 10A immunogenic conjugate comprises less than about 20% of free serotype 10A polysaccharide compared to the total amount of serotype 10A polysaccharide. In a preferred embodiment the serotype 10A immunogenic conjugate comprises less than about 15% of free serotype 10A polysaccharide compared to the total amount of serotype 10A polysaccharide.

In a preferred embodiment, the ratio (weight by weight) of serotype 10A polysaccharide to carrier protein in the conjugate is between 0.5 and 3. In a preferred embodiment, the ratio of serotype 10A polysaccharide to carrier protein in the conjugate is between 0.5 and 2, 0.5 and 1.5, 0.5 and 1, 1 and 1.5, 1 and 2. In a preferred embodiment, the ratio of serotype 10A polysaccharide to carrier protein in the conjugate is between 0.8 and 1.4. In a preferred embodiment, the ratio of serotype 10A capsular polysaccharide to carrier protein in the conjugate is between 0.8 and 1.2.

Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of Kd, columns are calibrated to establish the fraction at which molecules are fully excluded ($V_0$), (Kd=0), and the fraction representing the maximum retention ($V_i$), (Kd=1). The fraction at which a specified sample attribute is reached ($V_e$), is related to Kd by the expression, $Kd=(V_e-V_0)/(V_i-V_0)$.

In a preferred embodiment, at least 30% of the serotype 10A immunogenic conjugate has a Kd below or equal to 0.3 in a CL-4B column. In a preferred embodiment, at least 40% of the immunogenic conjugate has a Kd below or equal to 0.3 in a CL-4B column. In a preferred embodiment, at least 45%, 50%, 55%, 60%, 65%, 70%, 75%, 80%, or 85% of the serotype 10A immunogenic conjugate has a Kd below or equal to 0.3 in a CL-4B column. In a preferred embodiment, at least 60% of the serotype 10A immunogenic conjugate has a Kd below or equal to 0.3 in a CL-4B column. In a preferred embodiment, between 50% and 80% of the serotype 10A immunogenic conjugate has a Kd below or equal to 0.3 in a CL-4B column.

The degree of conjugation is the number of lysine residues in the carrier protein that are conjugated to the polysaccharide of interest. The evidence for lysine modification of the carrier protein, due to covalent linkages to the polysaccharides, is obtained by amino acid analysis using routine methods known to those of skill in the art. Conjugation results in a reduction in the number of lysine residues recovered, compared to the $CRM_{197}$ protein starting material used to generate the conjugate materials.

In a preferred embodiment, the degree of conjugation of the immunogenic conjugate is between 2 and 15, 2 and 13, 2 and 10, 2 and 8, 2 and 6, 2 and 5, 2 and 4, 3 and 15, 3 and 13, 3 and 10, 3 and 8, 3 and 6, 3 and 5, 3 and 4, 5 and 15, 5 an 10, 8 and 15, 8 and 12, 10 and 15 or 10 and 12. In a preferred embodiment, the degree of conjugation of the immunogenic conjugate is between 6 and 8.

Serotype 22F Immunogenic Conjugate

In a preferred embodiment, the immunogenic conjugate comprises at least 0.1, 0.2, 0.3, 0.4, 0.5, 0.6 or 0.7 or about 0.8 mM acetate per mM serotype 22F polysaccharide. In a preferred embodiment, the immunogenic conjugate comprises at least 0.5, 0.6 or 0.7 mM acetate per mM serotype 22F polysaccharide. In a preferred embodiment, the immunogenic conjugate comprises at least 0.6 mM acetate per mM serotype 22F polysaccharide. In a preferred embodiment, the immunogenic conjugate comprises at least 0.7 mM acetate per mM serotype 22F polysaccharide.

In a preferred embodiment, the ratio of mM acetate per mM serotype 22F polysaccharide in the immunogenic conjugate to mM acetate per mM serotype 22F polysaccharide in the isolated polysaccharide is at least 0.6, 0.65, 0.7, 0.75, 0.8, 0.85, 0.9, or 0.95. In a preferred embodiment, the ratio of mM acetate per mM serotype 22F polysaccharide in the immunogenic conjugate to mM acetate per mM serotype 22F polysaccharide in the isolated polysaccharide is at least 0.7. In a preferred embodiment, the ratio of mM acetate per mM serotype 22F polysaccharide in the immunogenic conjugate to mM acetate per mM serotype 22F polysaccharide in the isolated polysaccharide is at least 0.9.

In a preferred embodiment, the ratio of mM acetate per mM serotype 22F polysaccharide in the immunogenic conjugate to mM acetate per mM serotype 22F polysaccharide in the activated polysaccharide is at least 0.6, 0.65, 0.7, 0.75, 0.8, 0.85, 0.9, or 0.95. In a preferred embodiment, the ratio of mM acetate per mM serotype 22F polysaccharide in the immunogenic conjugate to mM acetate per mM serotype 22F polysaccharide in the activated polysaccharide is at least 0.7. In a preferred embodiment, the ratio of mM acetate per mM serotype 22F polysaccharide in the immunogenic conjugate to mM acetate per mM serotype 22F polysaccharide in the activated polysaccharide is at least 0.9.

In a preferred embodiment, the serotype 22F immunogenic conjugate has a molecular weight between 400 and 15000; 500 and 10000; 2000 and 10000 kDa; 3000 and 8000 kDa; or 3000 and 5000 kDa. In a preferred embodiment, the serotype 22F immunogenic conjugate has a molecular weight between 3000 and 5000 kDa. The molecular weight of the immunogenic conjugate is measured by SEC-MALLS.

In a preferred embodiment, the serotype 22F immunogenic conjugate comprises less than about 50, 45, 40, 35, 30, 25, 20 or 15% of free serotype 22F polysaccharide compared to the total amount of serotype 22F polysaccharide. In a preferred embodiment the serotype 22F immunogenic conjugate comprises less than about 40% of free serotype 22F polysaccharide compared to the total amount of serotype 22F polysaccharide. In a preferred embodiment the serotype 22F immunogenic conjugate comprises less than about 25% of free serotype 22F polysaccharide compared to the total amount of serotype 22F polysaccharide. In a preferred embodiment the serotype 22F immunogenic conjugate comprises less than about 20% of free serotype 22F polysaccharide compared to the total amount of serotype 22F polysaccharide. In a preferred embodiment the serotype 22F immunogenic conjugate comprises less than about 15% of free serotype 22F polysaccharide compared to the total amount of serotype 22F polysaccharide.

In a preferred embodiment, the ratio (weight by weight) of serotype 22F polysaccharide to carrier protein in the conjugate is between 0.5 and 3. In a preferred embodiment, the ratio of serotype 22F polysaccharide to carrier protein in the conjugate is between 0.5 and 2, 0.5 and 1.5, 0.8 and 1.2, 0.5 and 1, 1 and 1.5, or 1 and 2. In a preferred embodiment, the ratio of serotype 22F polysaccharide to carrier protein in the conjugate is between 0.8 and 1.2. In a preferred embodiment, the ratio of serotype 22F capsular polysaccharide to carrier protein in the conjugate is between 0.9 and 1.1.

In a preferred embodiment, at least 30% of the serotype 22F immunogenic conjugate has a Kd below or equal to 0.3 in a CL-4B column. In a preferred embodiment, at least 40% of the immunogenic conjugate has a Kd below or equal to 0.3 in a CL-4B column. In a preferred embodiment, at least 45%, 50%, 55%, 60%, 65%, 70%, 75%, 80%, or 85% of the serotype 22F immunogenic conjugate has a Kd below or equal to 0.3 in a CL-4B column. In a preferred embodiment, at least 60% of the serotype 22F immunogenic conjugate has a Kd below or equal to 0.3 in a CL-4B column. In a preferred embodiment, between 50% and 80% of the serotype 22F immunogenic conjugate has a Kd below or equal to 0.3 in a CL-4B column. In a preferred embodiment, between 65% and 80% of the serotype 22F immunogenic conjugate has a Kd below or equal to 0.3 in a CL-4B column.

In a preferred embodiment, the degree of conjugation of the immunogenic conjugate is between 2 and 15, 2 and 13, 2 and 10, 2 and 8, 2 and 6, 2 and 5, 2 and 4, 3 and 15, 3 and 13, 3 and 10, 3 and 8, 3 and 6, 3 and 5, 3 and 4, 4 and 7, 5 and 15, 5 an 10, 8 and 15, 8 and 12, 10 and 15 or 10 and 12. In a preferred embodiment, the degree of conjugation of the immunogenic conjugate is between 4 and 7.

Serotype 33F Immunogenic Conjugate

In a preferred embodiment, the immunogenic conjugate comprises at least 0.1, 0.2, 0.3, 0.4, 0.5, 0.6 or 0.7 or about 0.8 mM acetate per mM serotype 33F polysaccharide. In a preferred embodiment, the immunogenic conjugate comprises at least 0.5, 0.6 or 0.7 mM acetate per mM serotype 33F polysaccharide. In a preferred embodiment, the immunogenic conjugate comprises at least 0.6 mM acetate per mM serotype 33F polysaccharide. In a preferred embodiment, the immunogenic conjugate comprises at least 0.7 mM acetate per mM serotype 33F polysaccharide.

In a preferred embodiment, the ratio of mM acetate per mM serotype 33F polysaccharide in the immunogenic conjugate to mM acetate per mM serotype 33F polysaccharide in the isolated polysaccharide is at least 0.6, 0.65, 0.7, 0.75, 0.8, 0.85, 0.9, or 0.95. In a preferred embodiment, the ratio of mM acetate per mM serotype 33F polysaccharide in the immunogenic conjugate to mM acetate per mM serotype 33F polysaccharide in the isolated polysaccharide is at least 0.7. In a preferred embodiment, the ratio of mM acetate per mM serotype 33F polysaccharide in the immunogenic conjugate to mM acetate per mM serotype 33F polysaccharide in the isolated polysaccharide is at least 0.9.

In a preferred embodiment, the ratio of mM acetate per mM serotype 33F polysaccharide in the immunogenic conjugate to mM acetate per mM serotype 33F polysaccharide in the activated polysaccharide is at least 0.6, 0.65, 0.7, 0.75, 0.8, 0.85, 0.9, or 0.95. In a preferred embodiment, the ratio of mM acetate per mM serotype 33F polysaccharide in the immunogenic conjugate to mM acetate per mM serotype 33F polysaccharide in the activated polysaccharide is at least 0.7. In a preferred embodiment, the ratio of mM acetate per mM serotype 33F polysaccharide in the immunogenic conjugate to mM acetate per mM serotype 33F polysaccharide in the activated polysaccharide is at least 0.9.

In a preferred embodiment, the serotype 33F immunogenic conjugate has a molecular weight between 500 and 30000; 500 and 25000; 500 and 20000; 500 and 15000; 500 and 10000; 1000 and 10000; 1000 and 8000; 1000 and 5000; 2000 and 10000 kDa; 2000 and 8000; or 2000 and 5000 kDa. In a preferred embodiment, the serotype 33F immunogenic conjugate has a molecular weight between 1000 and 5000 kDa. The molecular weight of the immunogenic conjugate is measured by SEC-MALLS.

In a preferred embodiment, the serotype 33F immunogenic conjugate comprises less than about 50, 45, 40, 35, 30, 25, 20 or 15% of free serotype 33F polysaccharide compared to the total amount of serotype 33F polysaccharide. In a preferred embodiment the serotype 33F immunogenic conjugate comprises less than about 25% of free serotype 33F polysaccharide compared to the total amount of serotype 33F polysaccharide. In a preferred embodiment the serotype 33F immunogenic conjugate comprises less than about 20% of free serotype 33F polysaccharide compared to the total amount of serotype 33F polysaccharide. In a preferred embodiment the serotype 33F immunogenic conjugate comprises less than about 15% of free serotype 33F polysaccharide compared to the total amount of serotype 33F polysaccharide.

In a preferred embodiment, the ratio (weight by weight) of serotype 33F polysaccharide to carrier protein in the conjugate is between 0.4 and 3. In a preferred embodiment, the ratio of serotype 33F polysaccharide to carrier protein in the conjugate is between 0.5 and 2, 0.5 and 1.5, 0.5 and 1, 1 and 1.5, 1 and 2. In a preferred embodiment, the ratio of serotype 33F polysaccharide to carrier protein in the conjugate is between 0.5 and 1.5. In a preferred embodiment, the ratio of serotype 33F capsular polysaccharide to carrier protein in the conjugate is between 0.5 and 1.2.

In a preferred embodiment, at least 30% of the serotype 33F immunogenic conjugate has a Kd below or equal to 0.3 in a CL-4B column. In a preferred embodiment, at least 40% of the immunogenic conjugate has a Kd below or equal to 0.3 in a CL-4B column. In a preferred embodiment, at least 45%, 50%, 55%, 60%, 65% of the serotype 33F immunogenic conjugate has a Kd below or equal to 0.3 in a CL-4B column. In a preferred embodiment, at least 60% of the serotype 33F immunogenic conjugate has a Kd below or equal to 0.3 in a CL-4B column. In a preferred embodiment, between 40% and 80% of the serotype 33F immunogenic conjugate has a Kd below or equal to 0.3 in a CL-4B column. In a preferred embodiment, between 45% and 65% of the serotype 33F immunogenic conjugate has a Kd below or equal to 0.3 in a CL-4B column.

In a preferred embodiment, the degree of conjugation of the immunogenic conjugate is between 1 and 15, 2 and 13, 2 and 10, 2 and 8, 2 and 6, 2 and 5, 2 and 4, 3 and 15, 3 and 13, 3 and 10, 3 and 8, 3 and 6, 3 and 5, 3 and 4, 5 and 15, 5 an 10, 8 and 15, 8 and 12, 10 and 15 or 10 and 12. In a preferred embodiment, the degree of conjugation of the immunogenic conjugate is between 3 and 6.

Immunogenic Composition

The term "immunogenic composition" relates to any pharmaceutical composition containing an antigen, e.g., a microorganism or a component thereof, which composition can be used to elicit an immune response in a subject.

As used herein, "immunogenic" means an ability of an antigen (or an epitope of the antigen), such as a bacterial capsular polysaccharide, or a glycoconjugate or immunogenic composition comprising an antigen, to elicit an immune response in a host such as a mammal, either humorally or cellularly mediated, or both.

In a preferred embodiment, the immunogenic composition comprises a serotype 10A, 22F or 33F conjugate obtained by a process disclosed herein. In a preferred embodiment, the immunogenic composition comprising a serotype 10A, 22F or 33F conjugate obtainable by a process disclosed herein.

In an embodiment, the immunogenic composition disclosed herein, when administered to a subject, induces the formation of antibodies capable of binding to serotype 10A *Streptococcus pneumonia*. In an embodiment, the immunogenic composition disclosed herein, when administered to a subject, induces the formation of antibodies capable of binding to serotype 10A *Streptococcus pneumonia* as measured by a standard ELISA assay.

In an embodiment, the immunogenic composition disclosed herein, when administered to a subject, induces the formation of antibodies capable of killing serotype 10A *Streptococcus pneumonia* in an opsonophagocytosis assay as disclosed herein.

In an embodiment, the immunogenic composition disclosed herein, when administered to a subject, induces the formation of antibodies capable of binding to serotype 22F *Streptococcus pneumonia*. In an embodiment, the immunogenic composition disclosed herein, when administered to a subject, induces the formation of antibodies capable of binding to serotype 22F *Streptococcus pneumonia* as measured by a standard ELISA assay.

In an embodiment, the immunogenic composition disclosed herein, when administered to a subject, induces the formation of antibodies capable of killing serotype 22F *Streptococcus pneumonia* in an opsonophagocytosis assay as disclosed herein.

In an embodiment, the immunogenic composition disclosed herein, when administered to a subject, induces the formation of antibodies capable of binding to serotype 33F *Streptococcus pneumonia*. In an embodiment, the immunogenic composition disclosed herein, when administered to a subject, induces the formation of antibodies capable of binding to serotype 33F *Streptococcus pneumonia* as measured by a standard ELISA assay.

In an embodiment, the immunogenic composition disclosed herein, when administered to a subject, induces the formation of antibodies capable of killing serotype 33F *Streptococcus pneumonia* in an opsonophagocytosis assay as disclosed herein.

Formulation of the immunogenic composition of the present invention can be accomplished using art-recognized methods. For instance, the serotype 10A, 22F or 33F conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In a preferred embodiment, the immunogenic composition may comprise at least one additional antigen. In a preferred embodiment, the immunogenic composition may comprises at least one additional *Streptococcus pneumoniae* capsular polysaccharide.

In a preferred embodiment, the immunogenic composition may comprise at least one additional *Streptococcus pneumoniae* capsular polysaccharide conjugated to a carrier protein. In a preferred embodiment, said carrier protein is $CRM_{197}$.

In certain embodiments, the immunogenic composition comprises one or more adjuvants. As defined herein, an "adjuvant" is a substance that serves to enhance the immunogenicity of an immunogenic composition of this invention. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (PCT Pub. No. WO 90/14837), containing 5% Squalene, 0.5%5 Tween 80, and 0.5% Span 85 (optionally containing various amounts of MTP-PE (see below, although not required)) formulated into submicron particles using a microfluidizer such as Model 11OY microfluidizer (Microfluidics, Newton, Mass.), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);

(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(4) bacteriallipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy-4-Ophosphono-3-O—[(R)-3-tetradecanoyloxytetradecanoyl]-2-[(R)-3tetradecanoyloxytetradecanoylamino]-b-D-glucopyranoside, which is also know as 529 (formerly known as RC529), which is formulated as an aqueous form or as a stable emulsion, synthetic polynucleotides such as oligonucleotides containing CpG motif(s) (U.S. Pat. No. 6,207,646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules 87-1 and 87-2, etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an *E. coli* heat-labile toxin (LT), particularly LT-K63, LT-R72, CT-S109, PT-K9/G129 (see, e.g., WO 93/13302 and WO 92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acetyl-normuramyl-L-alanine-2-(1'-2'-dipalmitoyl-sn-glycero-3-hydroxyphosphoryloxy)-ethylamine (MTP-PE), etc.

In an embodiment of the present invention, the immunogenic compositions as disclosed herein comprise a CpG Oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

In an embodiment of the present invention, the immunogenic compositions as disclosed herein comprise any of the CpG Oligonucleotide described at pages 3 lines 22 to page 12 line 36 of WO2010/125480.

Different classes of CpG immunostimulatory oligonucleotides have been identified. These are referred to as A, B, C and P class, and are described in greater detail at pages 3 lines 22 to page 12 line 36 of WO2010/125480. Methods of the invention embrace the use of these different classes of CpG immunostimulatory oligonucleotides.

In an embodiment of the present invention, the immunogenic compositions as disclosed herein comprise an A class CpG Oligonucleotide. Preferably, the "A class" CpG oligonucleotide of the invention has the following nucleic acid sequence: 5' GGGGACGACGTCGTGGGGGGG 3' (SEQ ID NO: 1). Some non-limiting examples of A-Class oligonucleotides include: 5' G*G*G G A C G A C G T C G T G G*G*G*G*G*G 3' (SEQ ID NO: 2); wherein * refers to a phosphorothioate bond and _ refers to a phosphodiester bond.

In an embodiment of the present invention, the immunogenic compositions as disclosed herein comprise a B class CpG Oligonucleotide. In one embodiment, the CpG oligonucleotide for use in the present invention is a B class CpG oligonucleotide represented by at least the formula: 5' $X_1X_2CGX_3X_4$ 3', wherein $X_1$, $X_2$, $X_3$, and $X_4$ are nucleotides. In one embodiment, $X_2$ is adenine, guanine, or thymine. In another embodiment, $X_3$ is cytosine, adenine, or thymine.

The B class CpG oligonucleotide sequences of the invention are those broadly described above in U.S. Pat. Nos. 6,194,388, 6,207,646, 6,214,806, 6,218,371, 6,239,116 and 6,339,068. Exemplary sequences include but are not limited to those disclosed in these latter applications and patents.

In an embodiment, the "B class" CpG oligonucleotide of the invention has the following nucleic acid sequence:

```
                                    (SEQ ID NO: 3)
    5' TCGTCGTTTTTCGGTGCTTTT 3',
or
                                    (SEQ ID NO: 4)
    5' TCGTCGTTTTTCGGTCGTTTT 3',
or
                                    (SEQ ID NO: 5)
    5' TCGTCGTTTTGTCGTTTTGTCGTT 3',
or
                                    (SEQ ID NO: 6)
    5' TCGTCGTTTCGTCGTTTTGTCGTT 3',
or
                                    (SEQ ID NO: 7)
    5' TCGTCGTTTTGTCGTTTTTTTCGA 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

Some non-limiting examples of B-Class oligonucleotides include:

```
                                                    (SEQ ID NO: 8)
5' T*C*G*T*C*G*T*T*T*T*T*C*G*G*T*G*C*T*T*T*T 3',
or
                                                    (SEQ ID NO: 9)
5' T*C*G*T*C*G*T*T*T*T*T*C*G*G*T*C*G*T*T*T*T 3',
or
                                                    (SEQ ID NO: 10)
5' T*C*G*T*C*G*T*T*T*T*G*T*C*G*T*T*T*T*G*T*C*G*T*
T 3',
or
                                                    (SEQ ID NO: 11)
5' T*C*G*T*C*G*T*T*T*C*G*T*C*G*T*T*T*T*G*T*C*G*T*
T 3',
or
                                                    (SEQ ID NO: 12)
5' T*C*G*T*C*G*T*T*T*T*G*T*C*G*T*T*T*T*T*T*T*C*G*
A 3'.
``` wherein * refers to a phosphorothioate bond.

In an embodiment of the present invention, the immunogenic compositions as disclosed herein comprise a C class CpG Oligonucleotide. In an embodiment, the "C class" CpG oligonucleotides of the invention has the following nucleic acid sequence:

```
                                    (SEQ ID NO: 13)
    5' TCGCGTCGTTCGGCGCGCGCCG 3',
or
                                    (SEQ ID NO: 14)
    5' TCGTCGACGTTCGGCGCGCGCCG 3',
or
                                    (SEQ ID NO: 15)
    5' TCGGACGTTCGGCGCGCGCCG 3',
or
                                    (SEQ ID NO: 16)
    5' TCGGACGTTCGGCGCGCCG 3',
or
                                    (SEQ ID NO: 17)
    5' TCGCGTCGTTCGGCGCGCCG 3',
or
                                    (SEQ ID NO: 18)
    5' TCGACGTTCGGCGCGCGCCG 3',
or
                                    (SEQ ID NO: 19)
    5' TCGACGTTCGGCGCGCCG 3',
or
                                    (SEQ ID NO: 20)
    5' TCGCGTCGTTCGGCGCCG 3',
or
                                    (SEQ ID NO: 21)
    5' TCGCGACGTTCGGCGCGCGCCG 3',
or
                                    (SEQ ID NO: 22)
    5' TCGTCGTTTTCGGCGCGCGCCG 3',
or
                                    (SEQ ID NO: 23)
    5' TCGTCGTTTTCGGCGGCCGCCG 3',
or
                                    (SEQ ID NO: 24)
    5' TCGTCGTTTTACGGCGCCGTGCCG 3',
or
                                    (SEQ ID NO: 25)
    5' TCGTCGTTTTCGGCGCGCGCCGT 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide.

Some non-limiting examples of C-Class oligonucleotides include:

```
                                                    (SEQ ID NO: 26)
5' T*C_G*C_G*T*C_G*T*T*C_G*G*C*G*C_G*C*G*C*C*G 3',
or
                                                    (SEQ ID NO: 27)
5' T*C_G*T*C_G*A*C_G*T*T*C_G*G*C*G*C_G*C*G*C*C*
G 3',
or
                                                    (SEQ ID NO: 28)
5' T*C_G*G*A*C_G*T*T*C_G*G*C*G*C_G*C*G*C*C*G 3',
or
                                                    (SEQ ID NO: 29)
5' T*C_G*G*A*C_G*T*T*C_G*G*C*G*C*G*C*C*G 3',
or
                                                    (SEQ ID NO: 30)
5' T*C_G*C_G*T*C_G*T*T*C_G*G*C*G*C*G*C*C*G 3',
or
```

(SEQ ID NO: 31)
5' T*C_G*A*C_G*T*T*C_G*G*C*G*C_G*C*G*C*C*G 3',
or (SEQ ID NO: 32)
5' T*C_G*A*C_G*T*T*C_G*G*C*G*C*G*C*C*G 3',
or (SEQ ID NO: 33)
5' T*C_G*C_G*T*C_G*T*T*C_G*G*C*G*C*C*G 3',
or (SEQ ID NO: 34)
5' T*C_G*C_G*A*C_G*T*T*C_G*G*C*G*C_G*C*G*C*C*G 3',
or (SEQ ID NO: 35)
5' T*C*G*T*C*G*T*T*T*T*C*G*G*C*G*C*G*C*G*C*C*G 3',
or (SEQ ID NO: 36)
5' T*C*G*T*C*G*T*T*T*T*C*G*G*C*G*G*C*C*G*C*C*G 3',
or (SEQ ID NO: 37)
5' T*C*G*T*C_G*T*T*T*A*C_G*G*C*G*C*C_G*T*G*C*C* G 3',
or (SEQ ID NO: 38)
5' T*C_G*T*C*G*T*T*T*T*C*G*G*C*G*C*G*C*G*C*C*G* T 3' wherein * refers to a phosphorothioate bond and _refers to a phosphodiester bond. In any of these sequences, an ethyl-uridine or a halogen may substitute for the 5' T; examples of halogen substitutions include but are not limited to bromo-uridine or iodo-uridine substitutions.

In an embodiment of the present invention, the immunogenic compositions as disclosed herein comprise a P class CpG Oligonucleotide. In an embodiment, the CpG oligonucleotide for use in the present invention is a P class CpG oligonucleotide containing a 5' TLR activation domain and at least two palindromic regions, one palindromic region being a 5' palindromic region of at least 6 nucleotides in length and connected to a 3' palindromic region of at least 8 nucleotides in length either directly or through a spacer, wherein the oligonucleotide includes at least one YpR dinucleotide. In an embodiment, said oligoonucleotide is not T*C_G*T*C_G*A*C_G*T*T*T*C_G*G*C*G*C_G*C*G* C*C*G (SEQ ID NO: 27). In one embodiment the a P class CpG oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In yet another embodiment the TLR activation domain is within the 5' palindromic region. In another embodiment the TLR activation domain is immediately 5' to the 5' palindromic region.

In an embodiment, the "P class" CpG oligonucleotides of the invention has the following nucleic acid sequence: 5' TCGTCGACGATCGGCGCGCGCCG 3' (SEQ ID NO: 39).

In said sequences, all of the linkages may be all phosphorothioate bonds. In another embodiment, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

A non-limiting example of P-Class oligonucleotides include:

(SEQ ID NO: 40)
5' T*C_G*T*C_G*A*C_G*A*T*C_G*G*C*G*C_G*C*G*C*C* G 3' wherein * refers to a phosphorothioate bond and _refers to a phosphodiester bond. In one embodiment the oligonucleotide includes at least one phosphorothioate linkage. In another embodiment all internucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, all the internucleotide linkage of the CpG oligonucleotides disclosed herein are phosphodiester bonds ("soft" oligonucleotides, as described in the PCT application WO2007/026190). In another embodiment, CpG oligonucleotides of the invention are rendered resistant to degradation (e.g., are stabilized). A "stabilized oligonucleotide" refers to an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases.

The immunostimulatory oligonucleotides may have a chimeric backbone, which have combinations of phosphodiester and phosphorothioate linkages. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. When the phosphodiester linkage is preferentially located within the CpG motif such molecules are called "semi-soft" as described in the PCT application WO2007/026190.

The size of the CpG oligonucleotide (i.e., the number of nucleotide residues along the length of the oligonucleotide) also may contribute to the stimulatory activity of the oligonucleotide.

For facilitating uptake into cells, CpG oligonucleotide of the invention preferably have a minimum length of 6 nucleotide residues. Oligonucleotides of any size greater than 6 nucleotides (even many kb long) are capable of inducing an immune response if sufficient immunostimulatory motifs are present, because larger oligonucleotides are degraded inside cells. In certain embodiments, the CpG oligonucleotides are 6 to 100 nucleotides long, preferentially 8 to 30 nucleotides long. In important embodiments, nucleic acids and oligonucleotides of the invention are not plasmids or expression vectors.

In an embodiment, the CpG oligonucleotides disclosed herein comprise substitutions or modifications, such as in the bases and/or sugars as described at paragraph 134 to 147 of WO2007/026190.

In an embodiment, the CpG oligonucleotide of the present invention is chemically modified. Examples of chemical modifications are known to the skilled person and are described, for example in Uhlmann E. et al. (1990), Chem. Rev. 90:543, S. Agrawal, Ed., Humana Press, Totowa, USA 1993; Crooke, S. T. et al. (1996) Annu. Rev. Pharmacol.

Toxicol. 36:107-129; and Hunziker J. et al., (1995), Mod. Synth. Methods 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

In some embodiments of the invention, CpG-containing nucleic acids might be simply mixed with immunogenic carriers according to methods known to those skilled in the art (see, e.g. WO03/024480).

In a particular embodiment of the present invention, any of the immunogenic composition disclosed herein comprises from 2 μg to 100 mg of CpG oligonucleotide, preferably from 0.1 mg to 50 mg CpG oligonucleotide, preferably from 0.2 mg to 10 mg CpG oligonucleotide, preferably from 0.3 mg to 5 mg CpG oligonucleotide, even preferably from 0.5 to 2 mg CpG oligonucleotide, even preferably from 0.75 to 1.5 mg CpG oligonucleotide. In a preferred embodiment, the immunogenic composition disclosed herein comprises approximately 1 mg CpG oligonucleotide.

In a preferred embodiment, the adjuvant is an aluminum-based adjuvant selected from the group consisting of aluminum phosphate, aluminum sulfate and aluminum hydroxide. In one embodiment, the immunogenic compositions described herein comprise the adjuvant aluminum phosphate.

In a preferred embodiments, the immunogenic compositions of the invention further comprise at least one of a buffer, a cryoprotectant, a salt, a divalent cation, a non-ionic detergent, an inhibitor of free radical oxidation, a diluent or a carrier.

The immunogenic composition optionally can comprise a pharmaceutically acceptable carrier. Pharmaceutically acceptable carriers include carriers approved by a regulatory agency of a Federal, a state government, or other regulatory agency, or listed in the U.S. Pharmacopeia or other generally recognized pharmacopeia for use in animals, including humans as well as non-human mammals. The term carrier may be used to refer to a diluent, adjuvant, excipient, or vehicle with which the pharmaceutical composition is administered. Water, saline solutions and aqueous dextrose and glycerol solutions can be employed as liquid carriers, particularly for injectable solutions. Examples of suitable pharmaceutical carriers are described in "Remington's Pharmaceutical Sciences" by E. W. Martin. The formulation should suit the mode of administration.

The immunogenic composition optionally can comprise one or more physiologically acceptable buffers selected from, but not limited to Tris (trimethamine), phosphate, acetate, borate, citrate, glycine, histidine and succinate. In certain embodiments, the formulation is buffered to within a pH range of about 5.0 to about 7.0, preferably from about 5.5 to about 6.5.

The immunogenic composition optionally can comprise one or more non-ionic surfactants, including but not limited to polyoxyethylene sorbitan fatty acid esters, Polysorbate-80 (Tween 80), Polysorbate-60 (Tween 60), Polysorbate-40 (Tween 40) and Polysorbate-20 (Tween 20), polyoxyethylene alkyl ethers, including but not limited to Brij 58, Brij 35, as well as others such as Triton X-100; Triton X-114, NP40, Span 85 and the Pluronic series of non-ionic surfactants (e. g., Pluronic 121), with preferred components Polysorbate-80 at a concentration from about 0.001% to about 2% (with up to about 0.25% being preferred) or Polysorbate-40 at a concentration from about 0.001% to 1% (with up to about 0.5% being preferred).

The invention further relates to vaccines comprising the immunogenic composition of the invention.

Methods for Inducing an Immune Response and Protecting Against Infection

The present disclosure also includes methods of use for immunogenic compositions described herein. For example, one embodiment of the disclosure provides a method of inducing an immune response against Streptococcus pneumoniae, comprising administering to a subject an immunogenic amount of any of the immunogenic compositions described herein.

One embodiment of the disclosure provides a method of protecting a subject against an infection with Streptococcus pneumoniae, or a method of preventing infection with Streptococcus pneumoniae, or a method of reducing the severity of or delaying the onset of at least one symptom associated with an infection caused by Streptococcus pneumoniae, the methods comprising administering to a subject an immunogenic amount of any of the immunogenic compositions described herein.

One embodiment of the disclosure provides a method of protecting a subject against an infection with serotype 10A Streptococcus pneumoniae, or a method of preventing infection with serotype 10A Streptococcus pneumoniae, or a method of reducing the severity of or delaying the onset of at least one symptom associated with an infection caused by serotype 10A Streptococcus pneumoniae, the methods comprising administering to a subject an immunogenic amount of any of the immunogenic compositions described herein.

One embodiment of the disclosure provides a method of treating or preventing a Streptococcus pneumoniae infection, disease or condition associated with serotype 10A Streptococcus pneumoniae in a subject, the method comprising the step of administering a therapeutically or prophylactically effective amount of an immunogenic composition described herein to the subject. Another embodiment provides a method of treating or preventing a Streptococcus pneumoniae infection, disease or condition associated with a serotype 10A Streptococcus pneumoniae in a subject, the method comprising generating a polyclonal or monoclonal antibody preparation from the immunogenic composition described herein, and using said antibody preparation to confer passive immunity to the subject.

In one embodiment, the disclosure relates to the use of the immunogenic conjugate or immunogenic composition disclosed herein for the manufacture of a medicament for protecting a subject against an infection with Streptococcus pneumoniae, and/or preventing infection with Streptococcus pneumoniae, and/or reducing the severity of or delaying the onset of at least one symptom associated with an infection caused by Streptococcus pneumoniae, and/or protecting a subject against an infection with serotype 10A Streptococcus pneumoniae and/or preventing infection with serotype 10A Streptococcus pneumoniae, and/or reducing the severity of or delaying the onset of at least one symptom associated with an infection caused by serotype 10A Streptococcus pneumoniae.

One embodiment of the disclosure provides a method of protecting a subject against an infection with serotype 22F Streptococcus pneumoniae, or a method of preventing infection with serotype 22F Streptococcus pneumoniae, or a method of reducing the severity of or delaying the onset of at least one symptom associated with an infection caused by serotype 22F Streptococcus pneumoniae, the methods comprising administering to a subject an immunogenic amount of any of the immunogenic compositions described herein.

One embodiment of the disclosure provides a method of treating or preventing a *Streptococcus pneumoniae* infection, disease or condition associated with serotype 22F *Streptococcus pneumoniae* in a subject, the method comprising the step of administering a therapeutically or prophylactically effective amount of an immunogenic composition described herein to the subject. Another embodiment provides a method of treating or preventing a *Streptococcus pneumoniae* infection, disease or condition associated with a serotype 22F *Streptococcus pneumoniae* in a subject, the method comprising generating a polyclonal or monoclonal antibody preparation from the immunogenic composition described herein, and using said antibody preparation to confer passive immunity to the subject.

In one embodiment, the disclosure relates to the use of the immunogenic conjugate or immunogenic composition disclosed herein for the manufacture of a medicament for protecting a subject against an infection with *Streptococcus pneumoniae*, and/or preventing infection with *Streptococcus pneumoniae*, and/or reducing the severity of or delaying the onset of at least one symptom associated with an infection caused by *Streptococcus pneumoniae*, and/or protecting a subject against an infection with serotype 22F *Streptococcus pneumoniae* and/or preventing infection with serotype 22F *Streptococcus pneumoniae*, and/or reducing the severity of or delaying the onset of at least one symptom associated with an infection caused by serotype 22F *Streptococcus pneumoniae*.

One embodiment of the disclosure provides a method of protecting a subject against an infection with serotype 33F *Streptococcus pneumoniae*, or a method of preventing infection with serotype 33F *Streptococcus pneumoniae*, or a method of reducing the severity of or delaying the onset of at least one symptom associated with an infection caused by serotype 33F *Streptococcus pneumoniae*, the methods comprising administering to a subject an immunogenic amount of any of the immunogenic compositions described herein.

One embodiment of the disclosure provides a method of treating or preventing a *Streptococcus pneumoniae* infection, disease or condition associated with serotype 33F *Streptococcus pneumoniae* in a subject, the method comprising the step of administering a therapeutically or prophylactically effective amount of an immunogenic composition described herein to the subject. Another embodiment provides a method of treating or preventing a *Streptococcus pneumoniae* infection, disease or condition associated with a serotype 33F *Streptococcus pneumoniae* in a subject, the method comprising generating a polyclonal or monoclonal antibody preparation from the immunogenic composition described herein, and using said antibody preparation to confer passive immunity to the subject.

In one embodiment, the disclosure relates to the use of the immunogenic conjugate or immunogenic composition disclosed herein for the manufacture of a medicament for protecting a subject against an infection with *Streptococcus pneumoniae*, and/or preventing infection with *Streptococcus pneumoniae*, and/or reducing the severity of or delaying the onset of at least one symptom associated with an infection caused by *Streptococcus pneumoniae*, and/or protecting a subject against an infection with serotype 33F *Streptococcus pneumoniae* and/or preventing infection with serotype 33F *Streptococcus pneumoniae*, and/or reducing the severity of or delaying the onset of at least one symptom associated with an infection caused by serotype 33F *Streptococcus pneumoniae*.

An "immune response" to an immunogenic composition is the development in a subject of a humoral and/or a cell-mediated immune response to molecules present in the immunogenic composition or vaccine composition of interest. For purposes of the present disclosure, a "humoral immune response" is an antibody-mediated immune response and involves the induction and generation of antibodies that recognize and bind with some affinity for the antigen in the immunogenic composition or vaccine of the disclosure, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+ T helper cells or CD8+ cytotoxic T lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) *J. Immunol.* 151:4189-4199; and Doe et al. (1994) *Eur. J. Immunol.* 24:2369-2376.

As used herein, "treatment" (including variations thereof, e.g., "treat" or "treated") means any one or more of the following: (i) the prevention of infection or re-infection, as in a traditional vaccine, (ii) the reduction in the severity of, or, in the elimination of symptoms, and (iii) the substantial or complete elimination of the pathogen or disorder in question. Hence, treatment may be effected prophylactically (prior to infection) or therapeutically (following infection). In the present disclosure, prophylactic treatment is the preferred mode. According to a particular embodiment of the present disclosure, compositions and methods are provided that treat, including prophylactically and/or therapeutically immunize, a host animal against a serotype 10A *Streptococcus pneumoniae* infection. According to a particular embodiment of the present disclosure, compositions and methods are provided that treat, including prophylactically and/or therapeutically immunize, a host animal against a serotype 22F *Streptococcus pneumoniae* infection. According to a particular embodiment of the present disclosure, compositions and methods are provided that treat, including prophylactically and/or therapeutically immunize, a host animal against a serotype 33F *Streptococcus pneumoniae* infection. The methods of the present disclosure are useful for conferring prophylactic and/or therapeutic immunity to a subject. The methods of the present disclosure can also be practiced on subjects for biomedical research applications.

An "immunogenic amount," and "immunologically effective amount," both of which are used interchangeably herein, refers to the amount of antigen or immunogenic composition sufficient to elicit an immune response, either a cellular (T-cell) or humoral (B-cell or antibody) response, or both, as measured by standard assays known to one skilled in the art.

In a preferred embodiment, said subject is a human. In a most preferred embodiment, said subject is a newborn (i.e. under three months of age), an infant (from 3 months to one year of age) or a toddler (i.e. from one year to four years of age).

In an embodiment, the immunogenic compositions disclosed herein are for use as a vaccine.

In such embodiment, the subject to be vaccinated may be less than 1 year of age. For example, the subject to be vaccinated can be about 1, 2, 3, 4, 5, 6, 7, 8, 9, 10, 11 or 12 months of age. In an embodiment, the subject to be vaccinated is about 2, 4 or 6 months of age. In another embodiment, the subject to be vaccinated is less than 2 years of age. For example the subject to be vaccinated can be about 12-15 months of age. In some cases, as little as one dose of the immunogenic composition according to the invention is needed, but under some circumstances, a second, third or fourth dose may be given (see regimen section).

In an embodiment of the present invention, the subject to be vaccinated is a human adult 50 years of age or older, more preferably a human adult 55 years of age or older. In an embodiment, the subject to be vaccinated is a human adult 65 years of age or older, 70 years of age or older, 75 years of age or older or 80 years of age or older.

In an embodiment the subject to be vaccinated is an immunocompromised individual, in particular a human. An immunocompromised individual is generally defined as a person who exhibits an attenuated or reduced ability to mount a normal humoral or cellular defense to challenge by infectious agents.

In an embodiment of the present invention, the immunocompromised subject to be vaccinated suffers from a disease or condition that impairs the immune system and results in an antibody response that is insufficient to protect against or treat pneumococcal disease.

In an embodiment, said disease is a primary immunodeficiency disorder. Preferably, said primary immunodeficiency disorder is selected from the group consisting of: combined T- and B-cell immunodeficiencies, antibody deficiencies, well-defined syndromes, immune dysregulation diseases, phagocyte disorders, innate immunity deficiencies, autoinflammatory disorders, and complement deficiencies. In an embodiment, said primary immunodeficiency disorder is selected from the one disclosed on page 24 line 11 to page 25 line 19 of the PCT application WO2010/125480.

In a particular embodiment of the present invention, the immunocompromised subject to be vaccinated suffers from a disease selected from the groups consisting of: HIV-infection, acquired immunodeficiency syndrome (AIDS), cancer, chronic heart or lung disorders, congestive heart failure, diabetes mellitus, chronic liver disease, alcoholism, cirrhosis, spinal fluid leaks, cardiomyopathy, chronic bronchitis, emphysema, Chronic obstructive pulmonary disease (COPD), spleen dysfunction (such as sickle cell disease), lack of spleen function (asplenia), blood malignancy, leukemia, multiple myeloma, Hodgkin's disease, lymphoma, kidney failure, nephrotic syndrome and asthma.

In an embodiment of the present invention, the immunocompromised subject to be vaccinated suffers from malnutrition.

In a particular embodiment of the present invention, the immunocompromised subject to be vaccinated is taking a drug or treatment that lowers the body's resistance to infection. In an embodiment, said drug is selected from the one disclosed on page 26 line 33 to page 26 line 40 of the PCT application WO2010/125480.

In a particular embodiment of the present invention, the immunocompromised subject to be vaccinated is a smoker.

In a particular embodiment of the present invention, the immunocompromised subject to be vaccinated has a white blood cell count (leukocyte count) below $5 \times 10^9$ cells per liter, or below $4 \times 10^9$ cells per liter, or below $3 \times 10^9$ cells per liter, or below $2 \times 10^9$ cells per liter, or below $1 \times 10^9$ cells per liter, or below $0.5 \times 10^9$ cells per liter, or below $0.3 \times 10^9$ cells per liter, or below $0.1 \times 10^9$ cells per liter.

White blood cell count (leukocyte count): The number of white blood cells (WBCs) in the blood. The WBC is usually measured as part of the CBC (complete blood count). White blood cells are the infection-fighting cells in the blood and are distinct from the red (oxygen-carrying) blood cells known as erythrocytes. There are different types of white blood cells, including neutrophils (polymorphonuclear leukocytes; PMNs), band cells (slightly immature neutrophils), T-type lymphocytes (T cells), B-type lymphocytes (B cells), monocytes, eosinophils, and basophils. All the types of white blood cells are reflected in the white blood cell count. The normal range for the white blood cell count is usually between 4,300 and 10,800 cells per cubic millimeter of blood. This can also be referred to as the leukocyte count and can be expressed in international units as $4.3\text{-}10.8 \times 10^9$ cells per liter.

In a particular embodiment of the present invention, the immunocompromised subject to be vaccinated suffers from neutropenia. In a particular embodiment of the present invention, the immunocompromised subject to be vaccinated has a neutrophil count below $2 \times 10^9$ cells per liter, or below $1 \times 10^9$ cells per liter, or below $0.5 \times 10^9$ cells per liter, or below $0.1 \times 10^9$ cells per liter, or below $0.05 \times 10^9$ cells per liter.

A low white blood cell count or "neutropenia" is a condition characterized by abnormally low levels of neutrophils in the circulating blood. Neutrophils are a specific kind of white blood cell that help prevent and fight infections. The most common reason that cancer patients experience neutropenia is as a side effect of chemotherapy. Chemotherapy-induced neutropenia increases a patient's risk of infection and disrupts cancer treatment.

In a particular embodiment of the present invention, the immunocompromised subject to be vaccinated has a CD4+ cell count below $500/mm^3$, or CD4+ cell count below $300/mm^3$, or CD4+ cell count below $200/mm^3$, CD4+ cell count below $100/mm^3$, CD4+ cell count below $75/mm^3$, or CD4+ cell count below $50/mm^3$.

CD4 cell tests are normally reported as the number of cells in $mm^3$. Normal CD4 counts are between 500 and 1600, and CD8 counts are between 375 and 1100. CD4 counts drop dramatically in people with HIV.

In an embodiment of the invention, any of the immunocompromised subject disclosed herein is a human male or a human female.

The amount of a conjugate in a composition is generally calculated based on total polysaccharide, conjugated and non-conjugated for that conjugate. For example, a conjugate with 20% free polysaccharide will have about 80 mcg of conjugated polysaccharide and about 20 mcg of non-conjugated polysaccharide in a 100 mcg polysaccharide dose. The protein contribution to the conjugate is usually not considered when calculating the dose of a conjugate. Generally, each dose will comprise 0.1 to 100 mcg of polysaccharide, particularly 0.1 to 10 mcg, and more particularly 1 to 10 mcg and more particularly 1 to 5 µg. Preferably each dose will comprise about 1.1, 2, 2.2, 3, 3.3, 4, 4.4 µg of polysaccharide.

Optimal amounts of components for a particular immunogenic composition or vaccine can be ascertained by standard studies involving observation of appropriate immune responses in subjects. Following an initial vaccination, subjects can receive one or several booster immunizations adequately spaced.

The effectiveness of an antigen as an immunogen, can be measured either by proliferation assays, by cytolytic assays, such as chromium release assays to measure the ability of a T-cell to lyse its specific target cell, or by measuring the levels of B-cell activity by measuring the levels of circulating antibodies specific for the antigen in serum. An immune response may also be detected by measuring the serum levels of antigen specific antibody induced following administration of the antigen, and more specifically, by measuring the ability of the antibodies so induced to enhance the opsonophagocytic ability of particular white blood cells, as described herein. The level of protection of the immune response may be measured by challenging the immunized host with the antigen that has been administered. For example, if the antigen to which an immune response is desired is a bacterium, the level of protection induced by the immunogenic amount of the antigen is measured by detecting the percent survival or the percent mortality after challenge of the animals with the bacterial cells. In one embodiment, the amount of protection may be measured by measuring at least one symptom associated with the bacterial infection, e.g., a fever associated with the infection. The amount of each of the antigens in the multi-antigen or multi-component vaccine or immunogenic compositions will vary with respect to each of the other components and can be determined by methods known to the skilled artisan. Such methods would include procedures for measuring immunogenicity and/or in vivo efficacy.

The disclosure further provides antibodies and antibody compositions which bind specifically and selectively to the capsular polysaccharides or glycoconjugates of the present disclosure. In some embodiments, antibodies are generated upon administration to a subject of the capsular polysaccharides or glycoconjugates of the present disclosure. In some embodiments, the disclosure provides purified or isolated antibodies directed against one or more of the capsular polysaccharides or glycoconjugates of the present disclosure. In some embodiments, the antibodies of the present disclosure are functional as measured by killing bacteria in either an animal efficacy model or via an opsonophagocytic killing assay. In some embodiments, the antibodies of the disclosure confer passive immunity to a subject. The present disclosure further provides polynucleotide molecules encoding an antibody or antibody fragment of the disclosure, and a cell, cell line (such as hybridoma cells or other engineered cell lines for recombinant production of antibodies) or a transgenic animal that produces an antibody or antibody composition of the disclosure, using techniques well-known to those of skill in the art.

EXAMPLES

Example 1: Preparation of Serotype 22F Polysaccharide—$CRM_{197}$ Conjugate 1.1. Preparation of Isolated *Streptococcus pneumoniae* Serotype 22F Polysaccharide Serotype 22F capsular polysaccharides can be obtained directly from bacteria using isolation procedures known to one of ordinary skill in the art. (see for example methods disclosed U.S. Patent App. Pub. Nos. 20060228380, 20060228381, 20070184071, 20070184072, 20070231340, and 20080102498 or WO2008118752). The serotype 22F *Streptococcus pneumonia* were grown in a seed bottle and then transferred to a seed fermentor. Once the targeted optical density was reached, the cells were transferred to a production fermentor. The fermentation was broth was inactivated by the addition of N-lauroyl sarcosine and purified by ultrafiltration and diafiltration.

The purified *Streptococcus pneumoniae* serotype 22F polysaccharide was sized by high pressure homogenization using a PANDA 2K Homogenizer® (GEA Niro Soavi) to produce the isolated *Streptococcus pneumoniae* serotype 22F polysaccharide.

1.2. Oxidation of Isolated *Streptococcus pneumoniae* Serotype 22F Capsular Polysaccharide Oxidation of Polysaccharide was carried out in 100 mM potassium phosphate buffer (pH 5.8±0.2) obtained by sequential addition of calculated amount of 500 mM potassium phosphate buffer (pH 5.8) and WFI to give final polysaccharide concentration of 2.0 g/L. If required, the reaction pH was adjusted to 5.8, approximately. After pH adjustment, the reaction temperature was lowered to 5±3° C. Oxidation was initiated by the addition of 0.10±0.02 molar equivalents (MEq) of sodium periodate. The target oxidation reaction time is 16±1 hrs at 5±3° C.

The oxidation reaction was quenched with 2 MEq of 2,3-butanediol under continuous stirring at 5±3° C. for 1-2 hrs.

Concentration and diafiltration of the activated polysaccharide was carried out using 100K MWCO ultrafiltration cassettes. Diafiltration was performed against 35-fold diavolume of WFI. The purified activated polysaccharide was stored at 5±3° C. The purified activated saccharide is characterized inter alia by (i) Molecular Weight by SEC-MALLS (ii) presence of O-acetyl and (iii) Degree of Oxidation.

SEC-MALLS is used for the determination of the molecular weight of polysaccharides and polysaccharide-protein conjugates. SEC is used to separate the polysaccharides by hydrodynamic volume. Refractive index (RI) and multi-angle laser light scattering (MALLS) detectors are used for the determination of the molecular weight. When light interacts with matter, it scatters and the amount of scattered light is related to the concentration, the square of the do/dc (the specific refractive index increments), and the molar mass of the matter. The molecular weight measurement is calculated based on the readings from the scattered light signal from the MALLS detector and the concentration signal from the RI detector.

The degree of oxidation (DO=moles of sugar repeat unit/moles of aldehyde) of the activated polysaccharide was determined as follows:

The moles of sugar repeat unit is determined by various colorimetric methods, such as for example by using Anthrone method. The polysaccharide is first broken down to monosaccharides by the action of sulfuric acid and heat. The Anthrone reagent reacts with the hexoses to form a yellow-green colored complex whose absorbance is read spectrophotometrically at 625 nm. Within the range of the assay, the absorbance is directly proportional to the amount of hexose present.

The moles of aldehyde also is determined simultaneously, using MBTH colorimetric method. The MBTH assay involves the formation of an azine compound by reacting aldehyde groups (from a given sample) with a 3-methyl-2-benzothiazolone hydrazone (MBTH assay reagent). The excess 3-methyl-2-benzothiazolone hydrazone oxidizes to form a reactive cation. The reactive cation and the azine react to form a blue chromophore. The formed chromophore is then read spectroscopically at 650 nm.

1.3. Conjugation an Activated *Streptococcus pneumoniae* Serotype 22F Polysaccharide with $CRM_{197}$ The conjugation process consists of the following steps:
 a. Compounding with sucrose excipient, and lyophilization.
 b. Reconstitution of the lyophilized polysaccharide and $CRM_{197}$.
 c. Conjugation of activated polysaccharide to $CRM_{197}$ and capping
 d. Purification of the conjugate
 a. Compounding with Sucrose and Lyophilization The activated polysaccharide was compounded with sucrose (50% w/v in WFI) to a ratio of 25 grams of sucrose per gram of activated polysaccharide. The bottle of compounded mixture was then lyophilized. Following lyophilization, bottles containing lyophilized activated polysaccharide were stored at −20±5° C. Calculated amount of $CRM_{197}$ protein (target S/P input ratio=1) was shellfrozen and lyophilized separately. Lyophilized $CRM_{197}$ was stored at −20±5° C.

b. Reconstitution of Lyophilized Activated Polysaccharide and $CRM_{197}$ Protein Lyophilized activated polysaccharide was reconstituted in anhydrous dimethyl sulfoxide (DMSO). Upon complete dissolution of polysaccharide, an equal amount of anhydrous DMSO was added to lyophilized $CRM_{197}$ for reconstitution.

c. Conjugation of Activated Polysaccharide to $CRM_{197}$ and Capping

Reconstituted $CRM_{197}$ (in DMSO) was combined in the conjugation reaction vessel with the reconstituted activated polysaccharide. The final polysaccharide concentration in reaction solution is 1 g/L. Conjugation was initiated by adding 1.5±0.1 MEq of sodium cyanoborohydride to the reaction mixture and the reaction was incubated at 23±2° C. for 20±2 hrs. Termination of conjugation reaction is done by adding 2 MEq of sodium borohydride. The capping reaction was incubated at 23±2° C. for 3±1 hrs.

d. Purification of Conjugate

The conjugate solution was diluted 1:5 with chilled 5 mM succinate-0.9% saline (pH 6.0) in preparation for purification by tangential flow filtration using 100K MWCO membranes and a 20× diafiltration was performed using 5 mM succinate-0.9% saline (pH6.0) as the medium. After the diafiltration was completed, the conjugate retentate was further diluted, filtered through a 0.22 µm filter and stored at 2-8° C.

Table 1 comprises characterizing data for serotype 22F polysaccharide-$CRM_{197}$ conjugates obtained by the method of the invention. In particular, conjugates 5 and 6 of the table were obtained as disclosed in example 1.

Serotype 22F polysaccharide-$CRM_{197}$ conjugates generated by the RAC-DMSO process provided better yields and exhibited better batch to batch consistency in the MW along with significantly lower % Free saccharide levels and higher carrier protein (Lysine) modification compared to the conjugates generated by the RAC-aqueous process, as shown in Table 1.

TABLE 1

Serotype 22F Conjugates

| | Conjugate No | | | | | |
|---|---|---|---|---|---|---|
| | 1 Aqueous | 2 Aqueous | 3 Aqueous | 4 DMSO | 5 DMSO | 6 DMSO |
| Act Poly MW, kDa | 488 | 803 | 410 | 639 | 709 | 416 |
| DO | 17.3 | 15 | 10.3 | 14.6 | 14.4 | 13.7 |
| Input Ratio | 0.8 | 0.8 | 1 | 0.8 | 1 | 1 |
| % Conjugate Yield | 66 | 63 | 46 | 70 | 62 | 75 |
| % Free Saccharide | 18 | 43 | 45 | <5 | <5 | 8 |
| Conjugate MW | 1024 | 3544 | 462 | 3911 | 3734 | 4453 |
| Saccharide-Protein Ratio | 1.6 | 1.1 | 1.45 | 0.8 | 0.65 | 1.0 |
| Modified Lys (AAA) | 2.3 | N/A | N/A | 6.1 | N/A | 4.7 |

% Conjugate yield is calculated as follows: (amount of polysaccharide in the conjugate × 100)/amount of activated polysaccharide.

Example 2: Preparation of Serotype 10A Polysaccharide—$CRM_{197}$ Conjugate 2.1. Preparation of Isolated *Streptococcus pneumoniae* Serotype 10A Polysaccharide Isolated Serotype 10A polysaccharides was obtained as disclosed in example 1.1 except that the purified polysaccharide was not sized.

2.2. Oxidation of Isolated *Streptococcus pneumoniae* Serotype 10A Capsular Polysaccharide A calculated volume of 0.1M potassium phosphate buffer (pH 6.0) and water-for-injection (WFI) was added to the polysaccharide solution to achieve a final polysaccharide concentration of 2.5 g/L and a final concentration of 25 mM potassium phosphate buffer, If required pH was adjusted to 6.0, approximately. The diluted polysaccharide was then cooled to 5±3° C. Oxidation was initiated by the addition of 0.25±0.02 molar equivalents (MEq) of sodium periodate solution. The oxidation reaction time was approximately 4 hrs at 5±3° C. The oxidation reaction was quenched with 1 MEq of 2,3-butanediol under continuous stirring at 5±3° C. for 1-2 hrs.

After reaching the target reaction time, the activated polysaccharide was concentrated using 30K MWCO Millipore ultrafiltration cassettes. The diafiltration was then performed against 20-fold diavolume of WFI. The purified activated polysaccharide was stored at 5±3° C. The purified activated saccharide is characterized inter alia by (i) Molecular Weight by SEC-MALLS and (ii) Degree of Oxidation.

2.3 Conjugation an Activated *Streptococcus pneumoniae* Serotype 10A Polysaccharide with $CRM_{197}$ The conjugation process consists of the following steps:
 a. Compounding with sucrose excipient, and lyophilization.
 b. Reconstitution of the lyophilized polysaccharide and CRM197.

c. Conjugation of activated polysaccharide to CRM197 and capping d. Purification of the conjugate a. Compounding with Sucrose The activated polysaccharide is compounded with sucrose to a ratio of 25±2.5 grams of sucrose per gram of activated polysaccharide. The bottle of compounded mixture was then lyophilized. Following lyophilization, bottles containing lyophilized activated polysaccharide were stored at −20±5° C.

b. Reconstitution of Lyophilized Activated Polysaccharide and $CRM_{197}$ Protein Lyophilized activated polysaccharide was reconstituted in anhydrous dimethyl sulfoxide (DMSO). Upon complete dissolution of polysaccharide, the same amount of anhydrous DMSO was added to the calculated $CRM_{197}$ for reconstitution.

c. Conjugation of Activated Polysaccharide to $CRM_{197}$ and Capping

Reconstituted $CRM_{197}$ (in DMSO) was added to the reconstituted activated polysaccharide in the conjugation reactor. The final polysaccharide concentration is 1 g/L. Conjugation was performed by adding 1.2±0.1 MEq of sodium cyanoborohydride to the reaction mixture. The reaction was incubated and at 23±2° C. for 24±2 hrs. Termination of conjugation reaction is done by adding 2 MEq of sodium borohydride. The capping reaction was incubated at 23±2° C. for 3±1 hrs.

Termination of conjugation reaction is done by adding 2 MEq of sodium borohydride. This capping reaction proceeded for 3±1 hrs at 23±2° C.

d. Purification of Conjugate

The conjugate solution was then diluted into 5× (by volume) chilled 5 mM succinate-0.9% saline (pH 6.0 and a 20× diafiltration was performed using 5 mM succinate-0.9% saline (pH6.0). After the initial diafiltration was completed, the conjugate retentate was transferred through a 0.22 μm filter. The conjugate was diluted further with 5 mM succinate/0.9% saline (pH 6), and after the final 0.22 μm filtration step it was stored at 2-8° C.

Table 2 comprises characterizing data for serotype 10A polysaccharide-$CRM_{197}$ conjugates obtained by the method of the invention. In particular, conjugates 4 to 6 of table 2 were obtained as disclosed in example 2.

Serotype 10A polysaccharide-$CRM_{197}$ conjugates generated by the RAC-DMSO process provided better yields and exihibited better batch to batch consistency in the MW along with significantly lower % Free saccharide levels and higher carrier protein (Lysine) modification compared to the conjugates generated by the RAC-aqueous process, as shown in Table 2.

TABLE 2

Serotype 10A Conjugates

| | Conjugate No | | | | | |
|---|---|---|---|---|---|---|
| | 1 Aqueous | 2 Aqueous | 3 Aqueous | 4 DMSO | 5 DMSO | 6 DMSO |
| DO | 12.2 | 12.2 | 12.8 | 10.3 | 10.8 | 10.5 |
| Activated Saccharide MW, kda | 157 | 157 | 163 | 170 | 170 | 170 |
| Input Ratio | 1.0 | 1.0 | 1.0 | 1.1 | 1.1 | 1.1 |
| % Yield | 71 | 34 | 50 | 82 | 73 | 66 |
| % Free Saccharide | 20 | 31 | 26 | 6.8 | 6.4 | 9.7 |

TABLE 2-continued

Serotype 10A Conjugates

| | Conjugate No | | | | | |
|---|---|---|---|---|---|---|
| | 1 Aqueous | 2 Aqueous | 3 Aqueous | 4 DMSO | 5 DMSO | 6 DMSO |
| Conjugate MW, kDa | 1550 | 968 | 3050 | 4034 | 3463 | 5540 |
| Saccharide-protein ratio | 1.6 | 2.6 | 1.6 | 1.1 | 1.2 | 1.0 |
| Lys modification AAA | 2.6 | N/A | N/A | 6.9 | 6.7 | 6.1 |

Example 3: Preparation of Serotype 33F Polysaccharide—$CRM_{197}$ Conjugate 3.1. Preparation of Isolated *Streptococcus pneumoniae* Serotype 33F Polysaccharide Isolated Serotype 33F polysaccharide was obtained as disclosed in example 1.1.

3.2. Oxidation of Isolated *Streptococcus pneumoniae* Serotype 33F Capsular Polysaccharide A calculated volume of 0.1M sodium phosphate buffer (pH 6.0) and water-for-injection (WFI) was added to the polysaccharide solution to achieve a final polysaccharide concentration of 2 g/L. If required pH was adjusted to 6.0, approximately. The diluted polysaccharide was then cooled to 5±3° C. Oxidation was initiated by the addition of 0.1 molar equivalent (MEq) of sodium periodate solution. The oxidation reaction time was approximately 20 hrs at 5±3° C. The oxidation reaction was quenched with 1 MEq of 2,3-butanediol under continuous stirring at 5±3° C. for about 1 hour. After reaching the target reaction time, the activated polysaccharide was concentrated using 100K MWCO Millipore ultrafiltration cassettes. The diafiltration was then performed against 40-fold diavolume of WFI. The purified activated polysaccharide was stored at 5±3° C. The purified activated saccharide is characterized inter alia by (i) Molecular Weight by SEC-MALLS and (ii) Degree of Oxidation.

3.3 Conjugation an Activated *Streptococcus pneumoniae* Serotype 33F Polysaccharide with $CRM_{197}$ The serotype 33F polysaccharide-CRM197 conjugate was obtained by a process similar to the process of example 1.3, using the activated 33F polysaccharide obtained in example 3.2.

Serotype 33F polysaccharide-$CRM_{197}$ conjugates generated by the RAC-DMSO process provided better yields and exihibited better batch to batch consistency in terms of preservation of O-Acetyl levels along with overall lower % Free saccharide levels and higher carrier protein (Lysine) modification compared to the conjugates generated by the RAC-aqueous process, as shown in Table 3.

TABLE 3

Serotype 33F Conjugates

| | Conjugate No | | | | | |
|---|---|---|---|---|---|---|
| | 1 Aq | 2 Aq | 3 Aq | 4 DMSO | 5 DMSO | 6 DMSO |
| DO | 15.2 | 15.5 | 15.7 | 17 | 9 | 14 |
| Activated Poly MW | 1126 | 573 | 574 | 120 | 328 | 128 |

TABLE 3-continued

Serotype 33F Conjugates

| | Conjugate No | | | | | |
|---|---|---|---|---|---|---|
| | 1 Aq | 2 Aq | 3 Aq | 4 DMSO | 5 DMSO | 6 DMSO |
| % Yield | 65 | 51 | 48 | 78 | 86 | 66 |
| % Free Saccharide | 8.5 | 19 | 13 | 18 | 5 | <5 |
| Conjugate MW, kDa | 1341 | 2137 | 3674 | 3158 | 2165 | 2001 |
| Saccharide-protein ratio | 1.7 | 1.4 | 1.3 | 1.1 | 1.1 | 0.79 |
| % O—Ac preserved | <LOQ | <LOQ | <LOQ | 82 | 100% | 100% |
| Conj Lys (AAA) | N/A | 2.3 | 2.3 | 4.5 | 3.4 | 5.2 |

LOQ = Limit of Quantitation

Figure 4:
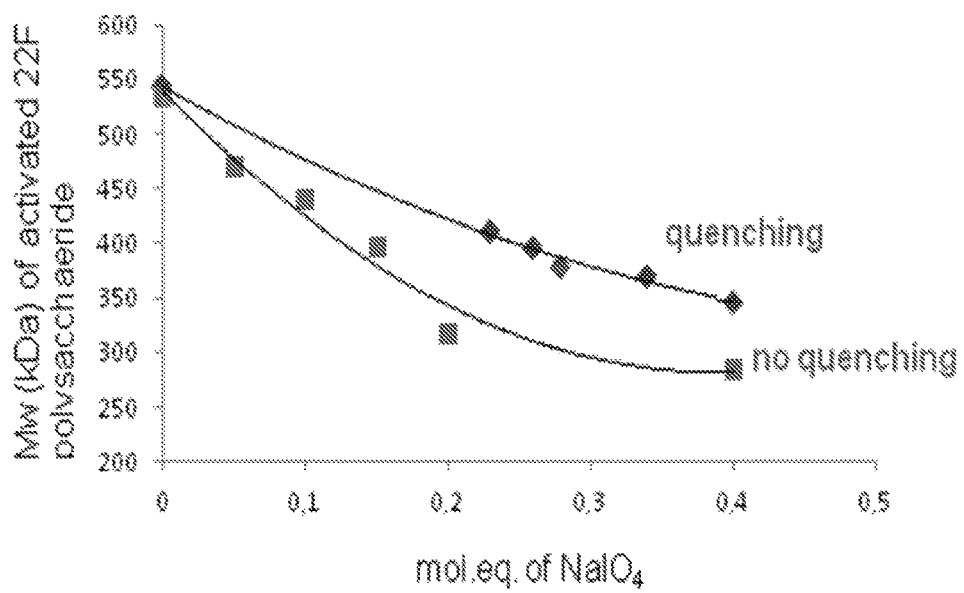
FIG. 4 shows the molecular weight of activated serotype 22F polysaccharide as a function of the amount of oxidizing agent at 23° C. with and without quenching step.
Figure 5:
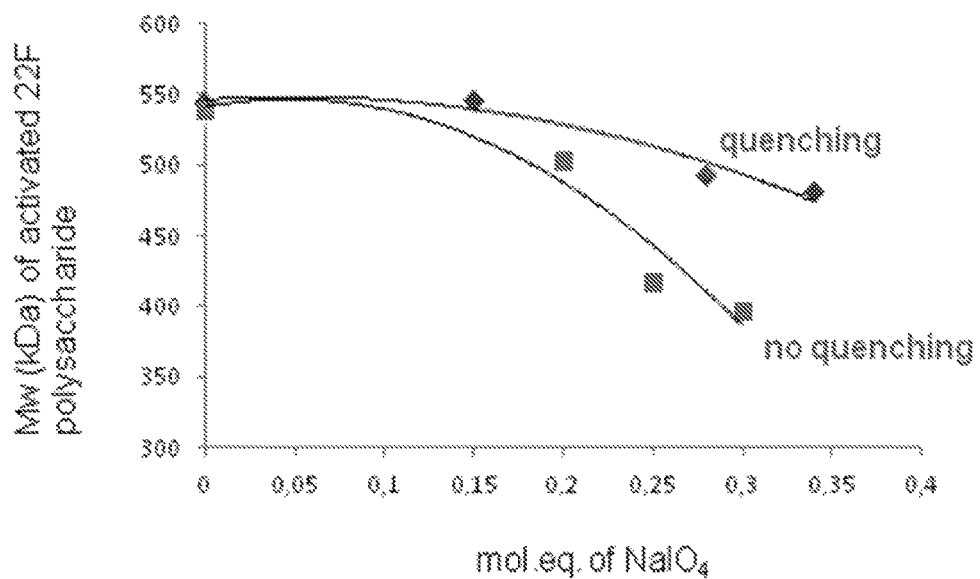
FIG. 5 shows the molecular weight of activated serotype 22F polysaccharide as a function of the amount of oxidizing agent at 4° C. with and without quenching step.
Figure 6:
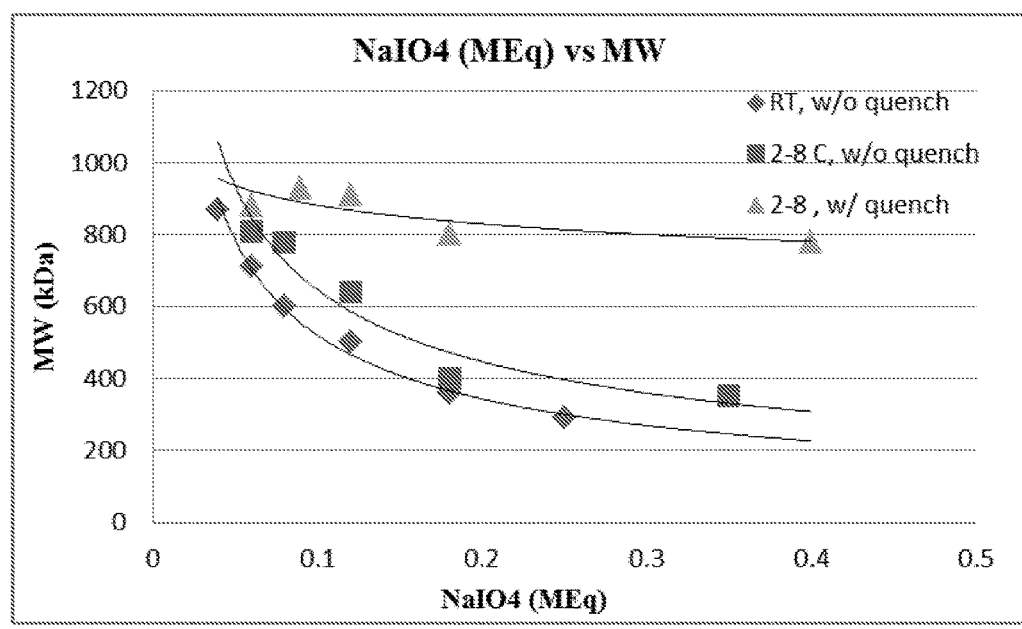
FIG. 6 shows the molecular weight of activated serotype 33F polysaccharide as a function of the amount of oxidizing agent at 2 to 8° C. with or without quenching step or at 23° C. without quenching step.

Example 4: Effect of Quenching on Molecular Weight of Activated Serotype 22F and 33F Polysaccharides Activation of 22F and 33F polysaccharides was carried out at either 4° C. or 22° C. Both temperatures gave similar DO values. However, due to the fact that elevated temperature resulted in faster breakdown of activated polysaccharide thereby lowering activated poly MW (as shown when comparing for example FIG. 4 (22° C.) and FIG. 5 (4° C.)), 4° C. was generally preferred for activation reaction. In addition, activation data showed that quenching of un-reacted $NaIO_4$ after oxidation is an essential step for activation, especially for activation using higher amount of $NaIO_4$. The graph shown in FIG. 6 indicate that the MW of the activated 33F polysaccharide is relatively stable when increasing concentrations of periodate are used for activation (with quenching) while such MW is highly variable when no quenching step is used. At specific conditions set up to obtain a targeted degree of oxidation, the molecular weight of the activated polysaccharide is less variable when the quenching step is used. Addition of quenching reagent after oxidation helps to keep the structural integrity of activated polysaccharide until the completion of purification for example by ultrafiltration and diafiltration.

Example 5: Opsonophagocytic Activity Assay (OPA)

The immunogenicity of the conjugates obtained by the processes disclosed herein can be assessed using the opsonophagocytic assay (OPA) described below.

Groups of thirty 6-7 week old female Swiss Webster mice were immunized with 0.001 µg, 0.01 µg, or 0.1 µg of test conjugates via the subcutaneous route on week 0. The mice were boosted with the same dose of conjugate on week 3 and then bled at week 4. Serotype-specific OPAs were performed on week 4 sera samples.

Validated opsonophagocytic activity (OPA) assays are used to measure functional antibodies in murine sera specific for *S. pneumonia* serotype 10A, 22F or 33F. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off.

OPA procedures were based on methods described in Hu et al., Clin Diagn Lab Immunol 2005; 12 (February (2)): 287-95 with the following modifications. Test serum was serially diluted 2.5-fold and added to microtiter assay plates. Live serotype 10A, 22F and 33F target bacterial strains were added to the wells and the plates were shaken at either 25° C. (serotype 22F) or 37° C. (serotype 10A and 33F) for 30 minutes. Differentiated HL-60 cells (phagocytes) and baby rabbit serum (3- to 4-week old, Pel-Freez®, 12.5% final concentration) were added to the wells, and the plates were shaken at 37° C. for 45 minutes (serotype 22F and 33F) or 60 minutes (serotype 10A). To terminate the reaction, 80 µL of 0.9% NaCl was added to all wells, mixed, and a 10 µL aliquot were transferred to the wells of MultiScreen HTS HV filter plates (Millipore®) containing 200 µL of water. Liquid was filtered through the plates under vacuum, and 150 µL of HySoy medium was added to each well and filtered through. The filter plates were then incubated at 37° C., 5% $CO_2$ overnight and were then fixed with Destain Solution (Bio-Rad). The plates were then stained with Coomassie Blue and destained once. Colonies were imaged and enumerated on a Cellular Technology Limited (CTL) ImmunoSpot Analyzer®. Raw colony counts were used to plot kill curves and calculate OPA titers.

Serotype 10A polysaccharide-$CRM_{197}$ conjugates, Serotype 22F polysaccharide-$CRM_{197}$ conjugates and Serotype 33F polysaccharide-$CRM_{197}$ conjugates obtained as disclosed in examples 1 to 3 were tested in the OPA assay disclosed above and were found to be immunogenic.

The invention claimed is:

1. A process for preparing an activated *Streptococcus pneumoniae* serotype 10A, 22F or 33F capsular polysaccharide, the process comprising the steps of:
   (a) reducing the size of a purified serotype 10A, 22F or 33F capsular polysaccharide using high pressure homogenization to yield an isolated serotype 10A, 22F or 33F capsular polysaccharide;
   (b) reacting the isolated serotype 10A, 22F or 33F capsular polysaccharide with an oxidizing agent; and
   (c) quenching the oxidation reaction of step (b) by adding a quenching agent to produce an activated *Streptococcus pneumoniae* serotype 10A, 22F or 33F polysaccharide.

2. A process according to claim 1 wherein the concentration of serotype 10A, 22F or 33F polysaccharide in step (a) is between 0.5 and 5 mg/mL.

3. A process according to claim 1 wherein said capsular polysaccharide is reacted with 0.05 to 0.3 molar equivalents of oxidizing agent in step (b).

4. A process according to claim 1 wherein the oxidizing agent is periodate.

5. A process according to claim 1 wherein the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

6. A process according to claim 1 wherein the oxidation reaction is quenched by the addition of 0.1 to 10, 0.5 to 5, 0.5 to 3 or 0.5 to 2 molar equivalents of quenching agent.

7. A process according to claim 1 wherein said isolated capsular polysaccharide is an isolated *Streptococcus pneumoniae* serotype 10A capsular polysaccharide.

8. A process according to claim 1 wherein said isolated capsular polysaccharide is an isolated *Streptococcus pneumoniae* serotype 22F capsular polysaccharide.

9. A process according to claim 1 wherein said isolated capsular polysaccharide is an isolated *Streptococcus pneumoniae* serotype 33F capsular polysaccharide.

* * * * *